(12) United States Patent
Gil Jiménez et al.

(10) Patent No.: US 12,378,170 B2
(45) Date of Patent: Aug. 5, 2025

(54) ALKANE DEHYDROGENATION NANOCATALYST AND PROCESS FOR ITS PREPARATION

(71) Applicant: FUNDACIÓ EURECAT, Cerdanyola del Vallès (ES)

(72) Inventors: Laia Gil Jiménez, Tarragona (ES); Isabel Vicente Valverde, Tarragona (ES); Aitor Gual Gozalbo, Tarragona (ES); Cyril Godard, Tarragona (ES); Carmen Claver Cabrero, Tarragona (ES)

(73) Assignee: FUNDACIÓ EURECAT, Cerdanyola del Vallès (ES)

( * ) Notice: Subject to any disclaimer, the term of this patent is extended or adjusted under 35 U.S.C. 154(b) by 77 days.

(21) Appl. No.: 18/278,610

(22) PCT Filed: Feb. 23, 2022

(86) PCT No.: PCT/EP2022/054574
§ 371 (c)(1),
(2) Date: Aug. 23, 2023

(87) PCT Pub. No.: WO2022/180125
PCT Pub. Date: Sep. 1, 2022

(65) Prior Publication Data
US 2024/0190795 A1    Jun. 13, 2024

(30) Foreign Application Priority Data
Feb. 24, 2021 (EP) .................................. 21382154

(51) Int. Cl.
*C07C 5/32* (2006.01)
*B01J 21/04* (2006.01)
(Continued)

(52) U.S. Cl.
CPC ............... *C07C 5/325* (2013.01); *B01J 21/04* (2013.01); *B01J 23/62* (2013.01); *B01J 23/626* (2013.01);
(Continued)

(58) Field of Classification Search
CPC ... C07C 5/325; C07C 2523/62; C07C 5/3337; B01J 21/04; B01J 23/62; B01J 23/626;
(Continued)

(56) References Cited

U.S. PATENT DOCUMENTS

| 2005/0003960 A1 | 1/2005 | Rytter et al. |
| 2008/0050641 A1* | 2/2008 | Dressick .............. B01J 31/1625 502/182 |

(Continued)

FOREIGN PATENT DOCUMENTS

| EP | 0328507 A1 | 8/1989 |
| WO | WO 2019/028018 A1 | 2/2019 |

OTHER PUBLICATIONS

International Search Report and Written Opinion mailed Jun. 8, 2022, for Application No. PCT/EP2022/054574; 3 pages.
(Continued)

*Primary Examiner* — Ali Z Fadhel
(74) *Attorney, Agent, or Firm* — Squire Patton Boggs (US) LLP

(57) ABSTRACT

The present invention relates to catalyst compositions comprising nanoparticles comprising one or more elements selected from a group 10 element, cocatalysts, catalyst promoters and organic molecules as organic stabilizing agents, in adequate porous supports. The invention also includes a particular mode of preparing the catalyst composition and the use of the catalyst in selective non-oxidative dehydrogenation of alkanes.

21 Claims, 4 Drawing Sheets

(51) Int. Cl.

| | |
|---|---|
| *B01J 23/62* | (2006.01) |
| *B01J 23/835* | (2006.01) |
| *B01J 31/24* | (2006.01) |
| *B01J 35/45* | (2024.01) |
| *B01J 35/61* | (2024.01) |
| *B01J 35/63* | (2024.01) |
| *B01J 37/02* | (2006.01) |
| *B01J 37/08* | (2006.01) |

(52) U.S. Cl.
CPC ......... *B01J 23/835* (2013.01); *B01J 31/2404* (2013.01); *B01J 35/45* (2024.01); *B01J 35/615* (2024.01); *B01J 35/635* (2024.01); *B01J 37/0203* (2013.01); *B01J 37/086* (2013.01); *B01J 2231/766* (2013.01); *B01J 2531/004* (2013.01); *B01J 2531/32* (2013.01); *B01J 2531/42* (2013.01); *B01J 2531/828* (2013.01); *B01J 2531/847* (2013.01); *C07C 2523/62* (2013.01)

(58) Field of Classification Search
CPC ...... B01J 23/835; B01J 31/2404; B01J 35/45; B01J 35/615; B01J 35/635; B01J 37/0203; B01J 37/086; B01J 2231/766; B01J 2351/004; B01J 2531/32; B01J 2531/42; B01J 2531/828; B01J 2531/847; B01J 2235/00; B01J 2235/15; B01J 2235/30; B01J 29/44; B01J 35/23; B01J 35/393; B01J 31/2269; B01J 31/1845; B01J 31/24
See application file for complete search history.

(56) References Cited

U.S. PATENT DOCUMENTS

| | | | | |
|---|---|---|---|---|
| 2015/0344667 | A1* | 12/2015 | Rao | C08K 3/36 524/847 |
| 2021/0178368 | A1* | 6/2021 | Gascon | B01J 35/45 |
| 2021/0252494 | A1* | 8/2021 | Ding | B01J 23/892 |

OTHER PUBLICATIONS

Bjørgen et al. (2008), Methanol to gasoline over zeolite H-ZSM-5: Improved catalyst performance by treatment with NaOH, Applied Catalysis A: General; published online Apr. 24, 2008; vol. 345, pp. 43-50.

Boualleg et al., "Unexpected, spontaneous and selective formation of colloidal Pt3Sn nanoparticles using organometallic Pt and Sn complexes", Chemical Communications; Jan. 1, 2010; vol. 46(26); pp. 4722-4724; XP055820268; ISSN 1359-7345; DOI 10.1039// C0CC00296h.

Castelbou et al., "New approach for the preparation of well defined Rh and Pt nanoparticles stabilized by phosphine-functionalized silica for selective hydrogenation reactions," Chemical Communications; Jan. 1, 2017; vol. 53(22); pp. 3261-3264; XP055820473; ISSN 1359-7345; DOI 10.1039//C6CC10338C.

Diaz de los Bernardos et al., "Facile synthesis of NHC-stabilized Ni nanoparticles and their catalytic application in the Z-selective hydrogenation of alkynes", Chemical Communications; Jan. 1, 2017; vol. 53(56); pp. 7894-7897; XP055820479; ISSN 1359-7345; DOI 10.1039//C7CC01779K.

Humblot et al., "Surface Organometallic Chemistry on Metals: Formation of a Stable :$Sn(n-C_4H_9)$ Fragment as a Precursor of Surface Alloy Obtained by Stepwise Hydrogenolysis of $Sn(n-C_4H_9)_4$ on a Platinum Particle Supported on Silica", Journal of American Chemical Society 1998; vol. 120(1); pp. 137-146.

Lomelí-Rosales et al. "A general one-pot methodology for the preparation of mono- and bimetallic nanoparticles supported on carbon nanotubes: application in the semi-hydrogenation of alkynes and acetylene," Chemistry A European Journal; Jun. 21, 2019; vol. 25(35); pp. 8321-8331; XP055820460; ISSN 0947-6539; 10.1002/chem.201901041.

Rouge et al., "A smarter approach to catalysts by design: Combining surface organometallic chemistry on oxide and metal gives selective catalysts for dehydrogenation of 2,3-dimethylbuthane", Molecular Catalysis; published online Apr. 19, 2019; vol. 471; pp. 21-26.

Sattler et al., "Catalytic Dehydrogenation of Light Alkanes on Metals and Metal Oxides", Chemical Reviews; Aug. 27, 2014; vol. 114; pp. 10613-10653.

Searles et al., "Highly Productive Propane Dehydrogenation Catalyst Using Silica-Supported Ga—Pt Nanoparticles Generated from Single-Sites", Journal of American Chemical Society 2018; vol. 140, pp. 11674-11679.

Wang et al. "Colloidal Synthesis of Pt—In Bimetallic nanoparticles for Propane Dehydrogenation", Can. J. Chem 2017; pp. 1-29.

Hu Zhong-Pan et al., "State-of-the-art catalysts for direct dehydrogenation of propane to propylene", Chinese Journal of Catalysis; Sep. 5, 2019; vol. 40; pp. 1233-1254.

* cited by examiner (A)

(B)

ALKANE DEHYDROGENATION NANOCATALYST AND PROCESS FOR ITS PREPARATION

CROSS-REFERENCE

The present application is a national-stage filing under 35 U.S.C. § 371 of International Patent Application No. PCT/EP2022/054574 (filed Feb. 23, 2022), which claims the benefit of European Patent Application No. 21382154.9 (filed Feb. 24, 2021), the contents of all of which are hereby incorporated by reference in their entirety for all purposes.

TECHNICAL FIELD

Present invention relates to the field of nanocatalysts for the non-oxidative dehydrogenation of alkanes to obtain light olefins and aromatics. It also relates to the valorization of light hydrocarbons mainly to be used in chemical industry.

BACKGROUND ART

Currently, the production of polymer building blocks, i.e., propene and butadiene, is carried out by cracking process of fossil naphtha. Cracking processes produce large $CO_2$ emissions due to its high-energy demanding nature (i.e., reaction temperatures 800-1200° C.). Recently, the dehydrogenation of light alkanes (C1-C8 alkanes) emerged as a more efficient and sustainable alternative for the production of polymer building blocks. To date, the non-oxidative dehydrogenation (nODH) process is applied at industrial scale with limited success due to technical limitations (i.e., the inefficient catalyst stability as well as thermodynamic limitations), economical limitations (i.e., high OPEX related with requirement of regeneration cycles due to the quick catalyst deactivation) and sustainability limitations (i.e., large Greenhouse gases (GHG) emissions associated with poor catalyst performances and catalyst regeneration process).

The current catalyst preparation process is for example described in the patent document EP0328507A1 (Fina Research). EP0328507 discloses a process for the catalytic dehydrogenation of propane, in the presence of hydrogen in a molar ratio of from 0.05 to 0.5 mole of hydrogen per mole of propane over a catalyst consisting of an alumina support containing at least one metal of the group 10 together with a cocatalyst and a promoter, which comprises the step of passing the feed to be dehydrogenated onto a catalyst containing from 0.2 to 1% by weight of platinum, from 0.15 to 1% by weight of tin as cocatalyst and from 0.8 to 2% by weight of potassium as promoter, said catalyst being obtained by submitting the alumina support containing the cocatalyst and calcined at a temperature comprised between 45° and 550° C., to a first treatment with a platinum compound, said first treatment being followed by a calcination in air and a reduction in the presence of hydrogen at a temperature comprised between 45° and 550° C.; then to an intermediate treatment to deposit potassium, said intermediate treatment being followed by a calcination at a temperature comprised between 38° and 550° C., and finally to a second treatment with a platinum compound, said second treatment being followed by a calcination at a temperature not exceeding 525° C., the dehydrogenation being carried out in the presence of said catalyst at a temperature comprised between 530° C. and 650° C., a pressure comprised between $5.0 \times 10^4$ Pa to $3.0 \times 10^5$ Pa and a weight hourly space velocity comprised between 1 and 10.

Some of the catalysts used in nODH are disclosed by Sattler et al, in a process commercially known as Oleflex (property of UOP-Honeywell). In this process, a catalyst that consists of nanoparticles of Pt (1 wt % of total catalyst) on alumina ($Al_2O_3$) support promoted with Na or K (0.1 wt % of total catalyst) and including also nanoparticles of Sn (1-2 wt % of the total catalyst) is used to dehydrogenate propane and isobutane at 520-705° C. and 1-3 bar. The catalysts allow a conversion (yield) from 22% to 70% of the alkanes, with a selectivity for propene within 70-90%. The reaction is carried out in a fluidized bed reactor consisting of three separate parts: several reactors in series, a product recovery station and a catalyst regeneration section. The catalyst lifetime is from 1 to 3 years and, for this reason, in the Oleflex process new catalyst is continuously added to the reactor system. With this method deposition of coke and sintering of Pt nanoparticles takes place, and at the same time catalyst particle attrition is an issue due to the fluidized bed. This requires that coke is to be depleted (by combustion) from the catalyst during regeneration, and chlorine is to be added to assist with Pt redispersion in this catalyst. (See Sattler et al. 2014. Catalytic Dehydrogenation of Light Alkanes on Metals and Metal Oxides. *Chemical Reviews vol. no.* 114, pp: 10613-10653).

Other nanocatalysts including Pt and an additional metal (i.e., Ga) for nODH of alkanes with higher selectivities for propene (around 98-99%) are also disclosed. For example, by Searles et al. (2018), that proposes the use of Ga—Pt nanocatalyst on $SiO_2$ providing high activity, selectivity and stability in propane nODH. The catalyst is prepared by surface organometallic chemistry approach and incipient wetness impregnation, and it yields a percentage of alkane conversion of around 32% and a selectivity for propene over 99% at 550° C. (see Searles et al. 2018. Highly Productive Propane Dehydrogenation Catalyst Using Silica-Supported Ga—Pt Nanoparticles Generated from Single-Sites. *Journal of American Chemical Society* 140, pp.: 11674-11679).

Most of these catalysts, however, lose their initial catalytic activity when in the regeneration cycle, since this regeneration cycle usually implies the use of aggressive conditions. In addition, the catalysts become damaged due to the high temperatures also used for converting propane and other alkanes to alkenes (i.e., propene), since alkane dehydrogenation is an endothermic reaction. Furthermore, coke formation takes place as a by-product reaction and it has to be burned off at high temperatures to regenerate the catalytic activity. Moreover, many of the catalysts are obtained by means of complex methods, including several steps and the involvement of sophisticated equipment and high temperatures.

Nanoparticles of Pt—In in solid support (SIRAL) useful for propane dehydrogenation catalysis are also disclosed to provide high conversion rates and selectivity for propene (See Wang et al. 2017. Colloidal Synthesis of Pt—In Bimetallic nanoparticles for Propane Dehydrogenation. *Can. J. Chem* 1-29). Wang et al. propose the colloidal synthesis of the bimetallic nanoparticles, in which polyvinylpyrrolidone (PVP) is used to obtain nanoparticles with homogeneous elemental distribution, controllable composition and narrow particle size distribution. The synthesis of the bimetallic nanoparticles is carried out by first mixing the support (SIRAL), the solvent (diethylene glycol) and the PVP; further heating the mixture at 220° C.; and then adding the organometallic precursors of the metals ($In(acac)_3$ and $Pt(acac)_2$) and let the mixture for certain time at 220° C. and then to cool it at 70° C. and maintain the reaction for 7 hours. As previously indicated, this method yields a catalyst with high conversion rates and selectivity. However, the use of PVP and other polymeric compounds for the preparation of nanoparticles of small particle size (1-2 nm) in colloidal suspension, imply large amounts of the polymers that then are to be removed from the nanoparticle surface. This makes the process of synthesis tedious and expensive. Another disadvantage of using polymeric compounds, such as PVP, is that due to the high temperatures employed for the conversion of alkanes to alkenes, coke is formed onto the surface of the catalyst, which becomes deactivated. Thus, regeneration for coke removal is to be performed at even higher temperatures (i.e. over 700° C.), which high temperatures may, on other ways, shorten the life of the catalyst.

Although good catalysts for nODH of alkanes have already been provided, there is still a need of additional ones with high catalytic conversion, activity and selectivity, and/or with a catalytic conversion. Catalytic conversion is measured as percentage of moles of dehydrogenated compounds per reactor pass per moles of compounds feed to the reactor (i.e., % mol/mol), maintained or slightly reduced along time of reaction. Catalytic activity is measured as the mole of substrate converted per mole of catalyst active site per unit of time (i.e., mol substrate converted×mol of catalyst active site$^{-1}$×h$^{-1}$). Catalytic selectivity is measured as percentage of moles of desired dehydrogenated compounds per reactor pass per total moles of transformed compounds (i.e., % mol/mol). Also are still needed catalysts with high selectivity, and whose obtention is reproducible and simple at acceptable costs.

SUMMARY OF INVENTION

Inventors propose new catalysts compositions or catalysts, comprising nanoparticles with metal elements on supports, to be used in the dehydrogenation of alkanes by nODH and also for aromatization of alkanes and cycloalkanes. These catalysts compositions can be defined as nanocatalysts (or nanocatalyst compositions), since they comprise nanoparticles. The catalysts compositions are, in particular, obtained by an also proposed by the inventors innovative nanofabrication approach, for the preparation of more homogeneous nanocatalysts compositions.

In addition, these catalysts are in some examples obtained by means of a one-pot reaction at relatively low temperatures (room temperature to 100° C.), thus making the process of synthesis/production more affordable and reproducible than other methods for obtaining similar catalysts. The catalyst compositions are homogeneous and have, in addition, nanoparticles of small size with a wide surface active area. Due to their composition, the catalysts are stable and maintain their catalytic activity in part because their surface is maintained clean (no impurities or deposition of products on their surface and resulting from the reaction they catalyze) for long periods of time.

Inventors surprisingly found that the selection of certain metals, and said metals in combination with other elements, all of them stabilized with particular organic compounds and adsorbed on porous supports, gave rise to highly active catalytic surface areas that, in addition, not only were selective for propene selectivity in nODH, but also that were highly stable and free of the main drawbacks of other catalysts for the same reaction (i.e. coke formation, by-side deactivating reactions, etc.).

Thus, a first aspect of the invention is a catalyst composition comprising:
(a) a metallic nanoparticle; and
(b) a porous support with a surface area; wherein the nanoparticle (a) is adsorbed on the surface area of the porous support;
wherein the nanoparticle (a) comprises (i) one or more metallic elements of group 10 of the periodic table; (ii) one or more organic molecules selected from the group consisting of an organophosphorus compound, and an N-heterocyclic carbene; and (iii) one or more metallic elements selected from the group consisting of tin (Sn), gallium (Ga), and indium (In).

Data below demonstrate that the new proposed catalyst compositions imply higher selectivities (>99%) than the commercial catalysts for the same reaction, even at similar conversion percentages or rates, which in some examples are also higher than the commercial ones. Moreover, as previously indicated, their catalytic activity is maintained for a longer period of time. Thus, conversion percentages are maintained or only slightly reduced during reaction.

Regarding some prior art catalysts proposals with also high selectivities (97-99%), the catalysts compositions of the present invention result from a simpler synthetic method than those of prior art, with only one step for their preparation, a part of being more reproducible. Reproducibility leads to more reliable catalysts.

Thus, the invention also discloses a reliable and reproducible method of synthesis of the catalysts compositions.

In a second aspect, the invention relates to a process for the preparation of a catalyst composition as defined above, comprising in a one-pot step, the decomposition of one or more organometallic precursor compounds of one or more elements of group 10, and of one or more organometallic precursors compounds of one or more metallic elements selected from the group consisting of tin (Sn), gallium (Ga), and indium (In), in the presence of an organic solvent, a porous support, and of one or more organic molecules selected from the group consisting of an organophosphorus compound and an N-heterocyclic carbene; the one-pot decomposition carried out at a temperature from 20° C. (r.t) to 100° C. for a period from 30 minutes to 70 hours, and at a pressure from $1.0 \times 10^5$ Pa to $5.0 \times 10^5$ Pa in hydrogen gas atmosphere.

As will be depicted in assays below, by means of this one-pot synthesis, the catalysts are highly active due to the small-variation of the surface areas (i.e., see Brunauer-Emmett-Teller (BET) values) respect to the pure support caused by the extremelly homogoneous distribution of the elements on the supports, and due to the synthesis at nanodimensions or nanosizes (nanofabrication) of well-dispersed nanoparticles of small sizes (1-15 nm, more particularly 1-5 nm), controlled by the presence of the organic molecule.

The catalyst composition may also be defined by its preparation process. Thus, it is also part of the present invention a catalyst composition comprising:
(a) a metallic nanoparticle; and
(b) a porous support with a surface area; wherein the nanoparticle (a) is adsorbed on the surface area of the porous support;
wherein the nanoparticle (a) comprises (i) one or more metallic elements of group 10 of the periodic table; (ii) one or more organic molecules selected from the group consisting of an organophosphorus compound, and an N-heterocyclic carbene; and (iii) one or more metallic elements selected from the group consisting of tin (Sn), gallium (Ga), and indium (In);
said catalyst composition obtainable by the decomposition, in a one-pot step, of one or more organometallic precursor compounds of one or more elements of group 10, and of one or more organometallic precursors compounds of one or more metallic elements selected from the group consisting of tin (Sn), gallium (Ga), and indium (In), in the presence of an organic solvent, a porous support, and of one or more organic molecules selected from the group consisting of an organophosphorus compound and an N-heterocyclic carbene; the one-pot decomposition carried out at a temperature from 20° C. (r.t) to 100° C. for a period from 30 minutes to 70 hours, and at a pressure from $1.0 \times 10^5$ Pa to $5.0 \times 10^5$ Pa in hydrogen gas atmosphere.

As previously indicated, the catalysts compositions are particularly useful in the dehydrogenation of alkanes to obtain alkenes. These catalysts are highly efficient and selective in the nODH of alkanes, mainly propane. The proposed catalyst compositions allow high yields or conversion rates of the alkanes to alkenes, mainly propene.

Thus, in a third aspect, the invention relates to a process for producing one or more $(C_2-C_4)$-alkenes, and/or one or more $(C_6)$-aromatic compounds, the process comprising a non-oxidative dehydrogenation of an $(C_2-C_4)$-alkane and/or $(C_3-C_4)$-alkene or, for the production of the one or more $(C_6)$-aromatic compounds, a non-oxidative dehydrogenation of an $(C_2-C_4)$-alkane and/or a non-oxidative dehydrogenation of a $(C_6)$-cycloalkane compound, said dehydrogenation carried out with a step of contacting a feed stream comprising the $(C_2-C_4)$-alkane and/or the $(C_3-C_4)$-alkene, or the $(C_2-C_4)$-alkane and/or the $(C_6)$-cycloalkane with the catalyst composition as defined in the first aspect, to obtain the one or more alkenes and the one or more aromatic compounds.

This third aspect includes the process for producing one or more $(C_2-C_4)$-alkenes by a non-oxidative dehydrogenation of an $(C_2-C_4)$-alkane or of an $(C_3-C_4)$-alkene that is further dehydrogenated, but also the production of one or more $(C_6)$-aromatic compounds, which aromatic compounds will result from the non-oxidative dehydrogenation of an $(C_2-C_4)$-alkane, but also from the non-oxidative dehydrogenation of a $(C_6)$-cycloalkane compound, if said $(C_6)$-cycloalkane compound is present in the feed stream composition which is contacted with the catalyst. For example, benzene can be produced either from two molecules of propane $(C_3H_8)$ that are dehydrogenated and condensate to give one molecule of benzene $(C_6H_6)$ and five hydrogen $(H_2)$ molecules; or from one molecule of cyclohexane $(C_6H_{12})$, which is dehydrogenated to obtain one molecule of benzene $(C_6H_6)$ and three hydrogen $(H_2)$ molecules.

Another aspect of the invention is the use of the catalyst composition as defined in the first aspect in a non-oxidative dehydrogenation of an alkane. Namely, the use of the catalyst composition as defined above in the first aspect, in non-oxidative propane dehydrogenation (PDH), non-oxidative butane-butene dehydrogenation (BDH), and propane aromatization.

DETAILED DESCRIPTION OF THE INVENTION

Figure 1:
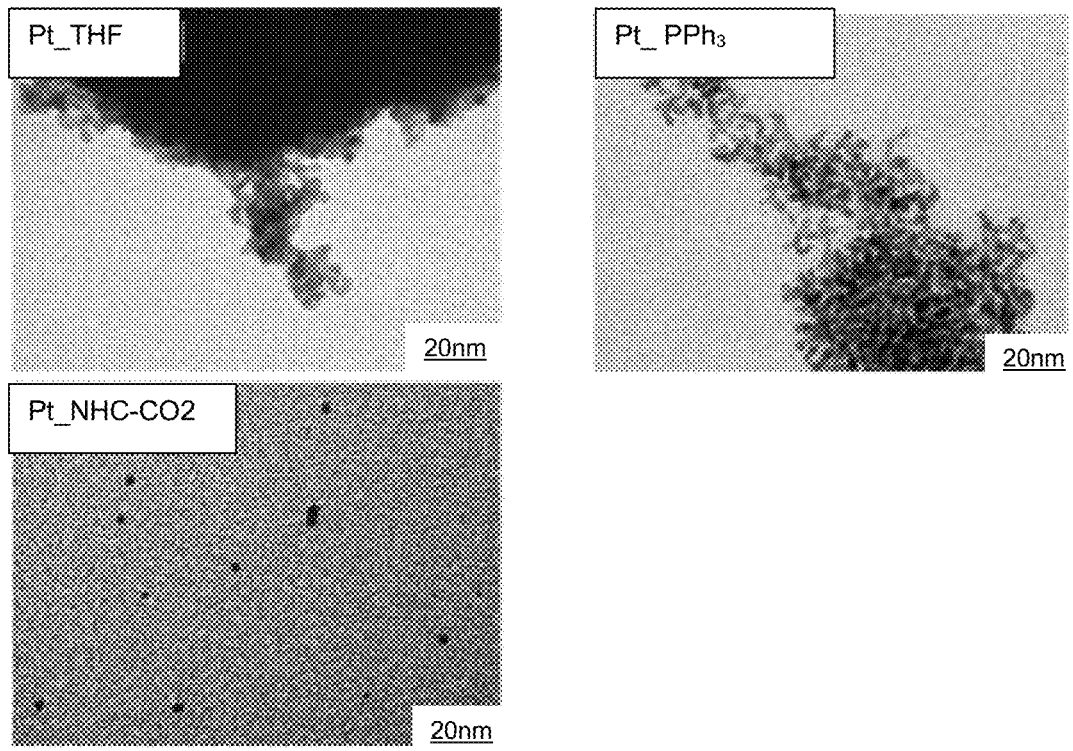
FIG. 1 shows Transmission Electronic Microscopy (TEM) images of Pt-NPs, prepared by organometallic approach in THF (the solvent, no organic stabilizing agent), or stabilized by $PPh_3$ and, NHC—$CO_2$, respectively. Size-reference 20 nm.

All terms as used herein in this application, unless otherwise stated, shall be understood in their ordinary meaning as known in the art. Other more specific definitions for certain terms as used in the present application are as set forth below and are intended to apply uniformly through-out the specification and claims unless an otherwise expressly set out definition provides a broader definition.

As used herein, the indefinite articles "a" and "an" are synonymous with "at least one" or "one or more." Unless indicated otherwise, definite articles used herein, such as "the" also include the plural of the noun.

The term "nanoparticle" as used herein (and abbreviated as NP for abbreviation purposes in this description), refers generally to a particle with at least two dimensions at the nanoscale, particularly with all three dimensions at the nanoscale (1-100 nm). In this description, the nanoparticles are in the range about 1.0 nm to about 15.0 nm. More in particular they are in the range from 1.0 nm to about 5.0 nm, even more particularly in the range from 1.0 to 3.0 nm. As regards the shape of the nanoparticles described herein, spherical and polyhedral nanoparticles are included. In a particular embodiment the nanoparticle is spherical.

As used herein, the term "size" refers to a characteristic physical dimension. For example, in the case of a nanoparticle that is substantially spherical, the size of the nanoparticle corresponds to the diameter of the nanoparticle. When referring to a set of nanoparticles as being of a particular size, it is contemplated that the set of nanoparticles can have a distribution of sizes around the specified size. Thus, as used herein, a size of a set of nanoparticles can refer to a mode of a distribution of sizes, such as a peak size of the distribution of sizes. In addition, when not perfectly spherical, the diameter is the equivalent diameter of the spherical body including the object.

When in this description the diameter/size of the nanoparticle is mentioned, it relates to the particle size measured by Transmission Electronic Microscopy (TEM). The size is also corroborated (verified) by X-ray diffraction (XRD).

As used herein, the term "catalyst composition" is understood to mean a composition consisting of the catalyst (active phase) and any other suitable components such as a catalyst support. The catalyst composition of the invention is for example suitable for the non-oxidative dehydrogenation of an alkane and for example particularly suitable for the non-oxidative dehydrogenation of propane. Also for abbreviation purposes in this description the catalyst compositions are also indicated as M-NPs, where M is the one or more metal (Pt, Pd, Ni, Sn, Ga, In) and NP stands for nanoparticle. Catalyst compositions can also be expressed as M-NPs@support, wherein @support indicates the particular porous (e.g. mesoporous) support employed to adsorb the metallic nanoparticles.

Throughout the description and claims, the terms ($C_2$-$C_4$)-alkene, shall be construed as straight or branched and encompass propylene, ethylene and butylene (But-1-ene, (2Z)-But-2-ene, (2E)-But-2-ene, 2-methylproppyl-1-ene. The term ($C_2$-$C_4$)-alkane shall be construed as straight or branched and encompass, in a particular embodiment, ethane, propane, butane (n-butane and isobutane). The term aromatic ($C_6$)-compounds shall be construed as a benzene optionally substituted with ($C_1$-$C_4$)-alkyl radicals or —OR1 radicals, being R1 selected from hydrogen (H) and ($C_2$-$C_4$)-alkyl, and encompass benzene, toluene, orto-, meta-, para-xylene. The term ($C_6$)-cycloalkane compounds relate to a cyclohexane optionally substituted with ($C_1$-$C_4$)-alkyl radicals or —OR1 radicals, R1 being selected from hydrogen (H) and ($C_1$-$C_4$)-alkyl, and encompasses cyclohexane, methylcyclohexane or orto-, meta-, paradimethylciclohexane. ($C_1$-$C_4$)-alkyl radicals are methyl, ethyl, propyl and butyl (n-butyl, isopropyl).

As indicated, the invention relates to catalyst compositions comprising:
(a) a metallic nanoparticle; and
(b) a porous support with a surface area; wherein the nanoparticle (a) is adsorbed on the surface area of the porous support;
wherein the nanoparticle (a) comprises (i) one or more metallic elements of group 10 of the periodic table; (ii) one or more organic molecules selected from the group consisting of an organophosphorus compound, and an N-heterocyclic carbene; and (iii) one or more metallic elements selected from the group consisting of tin (Sn), gallium (Ga), and indium (In).

The one or more organic molecules selected from the group consisting of an organophosphorus compound, and an N-heterocyclic carbene, are also referred in this description as "nanofabrication controlling agents", as "organic ligands" or as "organic stabilizing agents". They are organic compounds that are adsorbed onto the one or more metal atoms that will form part of a nanoparticle, in such a way that during the preparation process of the catalyst composition or once prepared, the said one or more element atoms will neither agglomerate nor coalescence with other nanoparticles of the surroundings and also including the element atoms and the said organic molecules selected from the group consisting of an organophosphorus compound, and an N-heterocyclic carbene. Thus, these organic compounds behave as nanofabrication controlling agents in the nanoparticles to avoid coalescence or agglomeration with other nanoparticles. This assures that the nanoparticles are small and well-dispersed in a predetermined volume or area. In addition, inventors also observed that the final composition of the nanoparticles (i.e., nanoparticle mean diameter and size distribution, shape and crystallinity (alloy and core-shell), well-distributed on the support, uniform compositions on different regions of the support and improved catalyst performance by control of the reactivity of the nanoparticle sites) was controlled by the presence of these organic molecules.

The presence of certain organic molecules (i.e., nanofabrication controlling agents) in nanoparticles has been previously disclosed for catalytic systems different than the ones of the invention and for a different reaction; the hydrogenation of alkynes to obtain alkenes, which is carried out at a temperature around 60° C. much lower than the alkane dehydrogenation (usually around 100° C.). See for example the catalysts comprising nanoparticles of nickel (Ni), copper (Cu) and palladium (Pd), or combination of these elements (Ni—Cu, Pd—Cu) stabilized with a C-coordinating N-heterocyclic carbene (NHC; or 1,3-dimethylimidazoliumcarboxylate) and obtained by decomposition of metallic precursors in a one-pot approach (see Lomelí-Rosales et al. 2019. A general one-pot methodology for the preparation of mono and bimetallic nanoparticles supported on carbon nanotubes: application in the semi-hydrogenation of alkynes and acetylene. Chem. Eur. J. 10.1002/chem.201901041).

However, it is widely accepted in the field of catalysts that each catalyst works for a particular reaction, and exchange of catalysts between reactions is usually senseless, since they do not work. Moreover, optimizations working for one of the catalysts do not work for others useful for the catalysis of very different reactions.

The term "organophosphorus compound", also referred in this description as "P-coordinating compound" relates to organic compounds comprising phosphorus (P). An example of organophosphorus compound are the phosphines. Phosphines (or phosphane) results from replacement of one or more hydrogen centers by an organic substituents R (alkyl, aryl) in $PH_3$ molecule, which gives $PH_{3-x}R_x$ (or $PR_1R_2R_3$ if all H are substituted), an organophosphine, generally referred to as phosphines, which can be primary, secondary, or tertiary phosphines depending on the number of hydrogen replacements. In the present invention, a particular and exemplified organophosphine is triphenylphosphine ($PPh_3$). General formula of phosphines is next depicted.

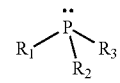

Phosphine

In a particular embodiment of the catalyst composition according to the first aspect, the organophosphorus compound is a compound of formula (I)

wherein n is an integer from 0 or 1, and when n is 1, Z is oxygen (═O); and wherein R1, R2 and R3 are each independently selected from:
($C_1$-$C_{10}$)-alkyl, in particular ($C_1$-$C_4$)-alkyl; ($C_1$-$C_4$)-alkoxyl; ($C_1$-$C_4$)-alkanoyl; ($C_1$-$C_4$)-alkoxycarbonyl and ($C_1$-$C_4$)-alkanoyloxy, all of them be construed as straight or branched,
phenyl optionally substituted, in particular substituted with ($C_1$-$C_4$)-alkyl and/or —OH groups;
a radical represented by —C—P(R4)(R5), being R4 and R5 independently selected from hydrogen (H), phenyl and phenyl optionally substituted;
a radical represented by —N(R6) (R7), being R6 and R7 independently selected from ($C_1$-$C_{10}$)-alkyl, in particular ($C_1$-$C_4$)-alkyl; ($C_1$-$C_4$)-alkoxyl; ($C_1$-$C_4$)-alkanoyl;

($C_1$-$C_4$)-alkoxycarbonyl and ($C_1$-$C_4$)-alkanoyloxy, all of them be construed as straight or branched; and a radical —O—R8, being R8 a $C_6$-aromatic ring optionally substituted.

When in formula (I) n is 0, the skilled person understands that Z is absent and then the organophosphorus compound of formula (I) has the pair of free electrons of the phosphorus (P) atom.

When in formula (I) at least one of R1 to R3 is a radical represented by —N(R6)(R7), the resulting organophosphorus compound is, indeed, a phosphoramidite. An example of a particular phosphoramidite is tris(dimethylamino)phosphine.

In another particular embodiment, the organophosphorus compound is selected from phosphines, as previously disclosed and including oxidized posphines (i.e., including-P=O group) and phosphoramidites (i.e., including at least onel —N(R6)(R7) radical), and phosphites.

Phosphites are to be understood as a salt of phosphorous acid, or as an uncharged ester of phosphorous acid containing or derived from the trivalent, negative radical PO3. Hydrogen Phosphite is an ion. Its chemical formula is $HPO_3^{2-}$. It contains phosphorus in its +3 oxidation state. The esters are compounds of formula below, being Rx, Rx' and Rx" equal or different radicals, such as ($C_1$-$C_{10}$) alkyl, or a C6-aromatic ring (for example phenyl):

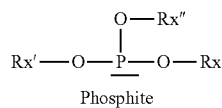

Phosphite

In another particular embodiment of the catalyst composition of the invention, the organophosphorus compound is a compound of formula (I), which is a phosphine in which n is an integer from 0 or 1, and when n is 1, Z is oxygen (=O); and wherein R1, R2 and R3 are each independently selected from:

($C_1$-$C_{10}$)-alkyl, in particular ($C_1$-$C_4$)-alkyl; ($C_1$-$C_4$)-alkoxyl; ($C_1$-$C_4$)-alkanoyl; ($C_1$-$C_4$)-alkoxycarbonyl and ($C_1$-$C_4$)-alkanoyloxy, all of them be construed as straight or branched, phenyl optionally substituted, in particular substituted with ($C_1$-$C_4$)-alkyl and/or —OH groups;

a radical represented by —C—P(R4)(R5), being R4 and R5 independently selected from hydrogen (H), phenyl and phenyl optionally substituted; and a radical represented by —N(R6)(R7), being R6 and R7 independently selected from ($C_1$-$C_{10}$)-alkyl, in particular ($C_1$-$C_4$)-alkyl; ($C_1$-$C_4$)-alkoxyl; ($C_1$-$C_4$)-alkanoyl; ($C_1$-$C_4$)-alkoxycarbonyl and ($C_1$-$C_4$)-alkanoyloxy, all of them be construed as straight or branched.

In a more particular embodiment, the phosphine is selected from the group consisting of triphenylphosphine, 1,2-bis(diphenylphosphino)methane, tris(dimethylamino) phosphine, diphenylphosphine oxide, and trioctylphosphine oxide, and combinations thereof.

On the alternative and in another particular embodiment of the catalyst composition according to the invention, the organophosphorus compound is a compound of formula (I), which is a phosphite in which n is 0 and wherein R1, R2 and R3 are each a radical —O—R8, being R8 a $C_6$-aromatic ring optionally substituted, in particular substituted with particular ($C_1$-$C_4$)-alkyl.

In even a more particular embodiment, the compound of formula (I) is the phosphite triphenylphosphite.

Thus, in other words, in a particular embodiment of the catalyst composition of the first aspect, the organic molecules are selected from an N-heterocyclic carbene, and an organophosphorous compound selected from phosphites and phosphines, the later including oxidized posphines and phosphoramidites. In particular, the organophosphorus compound is selected from the group consisting of triphenylphosphine, 1,2-bis(diphenylphosphino)methane, tris(dimethylamino)phosphine, diphenylphosphine oxide, and trioctylphosphine oxide, triphenylphosphite, and combinations thereof. The chemical formulas of the previous list including phosphines and phosphites are illustrated below:

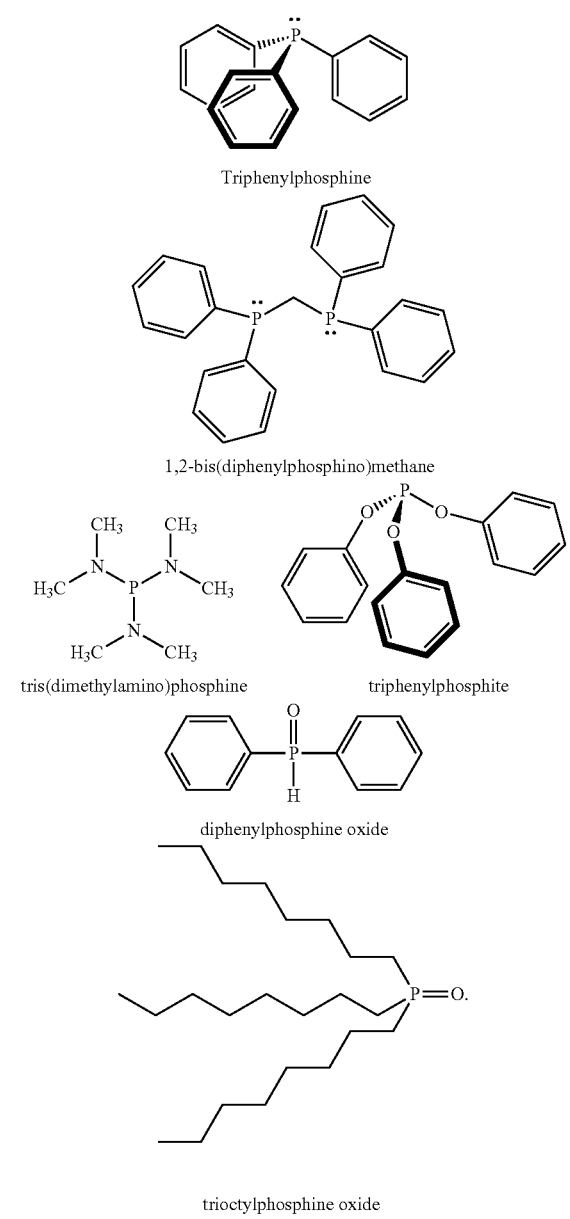

The term "alkyl", includes ($C_1$-$C_4$)-alkyl, ($C_1$-$C_{10}$)-alkyl, ($C_1$-$C_4$)-alkoxyl, ($C_1$-$C_4$)-alkanoyl, ($C_1$-$C_4$)-alkoxycarbonyl and ($C_1$-$C_4$)-alkanoyloxy, all of them be construed as straight or branched. Examples of ($C_1$-$C_{10}$)-alkyl are methyl, ethyl, propyl, isopropyl, butyl, n-butyl, isobutyl, tert-butyl, n-pentyl, n-hexyl, n-hepyl, n-octyl, n-nonyl and n-decenyl. The term "aryl" refers to a radical of one ring system with 1-3 rings, the rings being aromatic and being isolated or partially/totally fused and having 5-6 members, being each member independently selected from C, CH, N, NH, O, S where chemically possible, and the ring system being optionally substituted by one or more radicals independently selected from the group consisting of ($C_1$-$C_6$) alkyl, ($C_1$-$C_6$) alkoxy, nitro, cyano, and halogen. Examples of aryl radicals include phenyl and benzyl.

The "C-coordinating N-heterocyclic carbenes", also referred in this description as "carbon adducts of N-heterocyclic carbenes" are carbenes of formula $RN_2C$:, where the 'R' is a ($C_2$-$C_n$)-alkyl forming with the two N atoms an heterocycle, and the C atom coordinates (i.e. adducts) with another carbon atom containing compound (i.e. a carbon dioxide). The carbon dioxide adducts of N-heterocyclic carbenes reacts under the reactions conditions used for the catalyst preparation forming N-heterocyclic carbene ($RN_2C$:) and another carbon atom containing compound (i.e., carbon dioxide). In the present invention, a particular and exemplified carbon adducts of N-heterocyclic carbenes is the 1,3-dimethylimidazoliumcarboxylate (NHC—$CO_2$), illustrated below, and which gives the 1,3-dimethylimidazoliumcarbene.

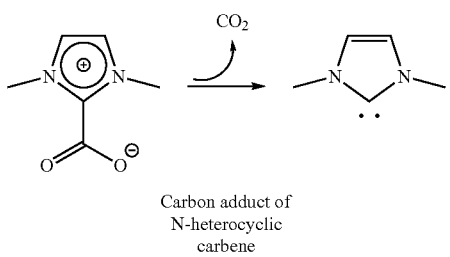

Carbon adduct of
N-heterocyclic
carbene

The metals of group 10 are nickel (Ni), palladium (Pd) and platinum (Pt). These elements are, as such, the atoms that catalyze the reaction. In a particular embodiment of the catalyst composition, the nanoparticle (a) comprises at least platinum (Pt) or nickel (Ni). In another particular embodiment of the first aspect, the nanoparticle comprises a combination of Pt and/or Ni with Pd.

The one or more metallic elements selected from the group consisting of tin (Sn), gallium (Ga), and indium (In) are cocatalysts in the catalyst composition. Thus, they also increase the rate of the chemical reaction catalyzed by the metallic elements of the group 10 in the nanoparticle, and cooperate improving each other catalytic activity (better yield and/or selectivity).

In a particular embodiment of the first aspect, optionally in combination with any embodiment above or below, the one or more of the tin (Sn), gallium (Ga) and indium (In) are in the nanoparticles (a), and onto the surface area of the porous support (b). Indeed, any of these cocatalysts are, in particular, conforming the nanoparticle (a), mainly adsorbed onto a surface area of a primary nanoparticle (a') conformed only by the one or more metallic elements of group 10, and they are also onto the surface area of the porous support (b). Thus, the catalyst compositions comprise:
(a) nanoparticles comprising the metallic element of group 10, the one or more of the cocatalysts, and the one or more of the organic molecules selected from the group consisting of an organophosphorus compound and an N-heterocyclic; and
(b) the porous support comprising, adsorbed on its surface, nanoparticles and also the one or more cocatalysts independent of the nanoparticle (i.e., not forming part of the nanoparticle).

In yet another particular embodiment the nanoparticle of the catalyst composition comprises two of, or the three elements (i.e., cocatalysts) selected from Sn, Ga and In.

In another particular embodiment of the catalyst composition of the first aspect, optionally in combination with previous and further embodiments, the said composition further comprises one or more catalyst promoters which, in particular are alkaline elements, more in particular selected from lithium (Li) and sodium (Na).

Promoters are substances or elements added to solid catalyst compositions to improve its performance in a chemical reaction. The promoters enhance the action of the catalyst (efficiency), but they do not have any catalytic activity.

The nanoparticles in the catalyst composition have a diameter from lower than 1.0 nm to 15 nm. In particular from 0.5 nm to 15 nm, and more in particular from 1.0 to 15.0 nm (e.g. 1.0, 2.0, 3.0, 4.0, 5.0, 6.0, 7.0, 8.0, 9.0, 10.0, 11.0, 12.0, 13.0, 14.0, and 15.0). Nanoparticles comprising Ni as only element of group 10, and Sn and/or Ga have a diameter from 10.0 nm to 15.0 nm.

Nanoparticles comprising Pt have diameter sizes from 1.0 nm to 5.0 nm. In general, the smaller the size of the nanoparticles, the better the performance of the catalyst because the dispersion of the number of available active metal sites is maximized. This results in a more efficient use of the precious metals. Thus, in another particular embodiment of the catalysts according to the first aspect, the nanoparticles have a diameter from 1.0-5.0 nm, including 1.0, 2.0, 3.0, 4.0, 5.0. More in particular from 1.0 to 3.0 nm, including 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0; and even more in particular the diameter is from 1.0 to 2.0 nm. All these diameters of the nanoparticles relate to the ones determined by TEM, as will be illustrated in examples below.

In another also particular embodiment, the catalyst composition according to the first aspect has a specific surface area (in m2/g), according to BET theory, from 100 to 500 m2/g.

As used herein, the BET surface area is determined by nitrogen ($N_2$) adsorption techniques (ASTM D-3663-03, ASTM International, October 2003, or ISO 9277 standard for calculating the specific surface area of solids is based on the BET method). Brunauer-Emmett-Teller (BET) theory aims to explain the physical adsorption of gas molecules on a solid surface and serves as the basis for an important analysis technique for the measurement of the specific surface area of materials. In the field of solid catalysis, the surface area of catalysts is an important factor in catalytic activity.

In another particular embodiment, in the catalyst composition according to the first aspect, the mole ratio of the one or more organic molecules and the one or more of the total metallic elements is of 0.05-0.25:1.Determination of mole ratio is, for example, carried out by X-ray photoelectron spectroscopy measuring the bands corresponding to P, N or C in relation with the metal bands. Usually, each nanoparticle contains 30-40 metal atoms and the nanoparticle contains 5-10 organic molecules acting as stabilizer of the nanoparticle.

Also another particular embodiment of the catalyst composition, optionally in combination with any of the catalyst composition embodiments above or below, is that the porous support is selected from alumina-based, silica-based, mesoporous zeolites-based and related aluminosilicates. According to the IUPAC definition, solids that contain pores with pore diameter (i)>50 nm are called as macro-porous, (ii) between 1-50 nm are mesoporous and (iii)<1 nm are microporous. In a particular embodiment of the catalyst composition, optionally in combination with any of the embodiments above or below, the support is a mesoporous support.

The term "alumina-based" means that the porous support mainly comprises or consists of alumina ($Al_2O_3$). For analogy, "silica-based" means that the mesoporous support mainly comprises or consists of silica ($SiO_2$). In the same way, the expression "zeolites-based and related aluminosilicates" means that the porous support mainly comprises or consists on aluminosilicates of several chemical formulas.

When alumina is selected, it is in particular from the list consisting of the gamma-$Al_2O_3$ and theta-$Al_2O_3$ and the promoted alumina with alkaline elements (Li—$Al_2O_3$ and Na—$Al_2O_3$). Methods for preparing these alumina supports are for example disclosed in the research of Rouge et al. (2019). A smarter approach to catalysts by design: Combining surface organometallic chemistry on oxide and metal gives selective catalysts for dehydrogenation of 2,3-dimethylbuthane. *Molecular Catalysis* 471, 21-26. (see in more detailed in Examples section).

In a more particular embodiment, zeotype (in particular ZSM-5 zeolites) are materials without acid sites, or with only a small number of acid sites that have been selected for reactions targeting propane dehydrogenation (PDH) and butane dehydrogenation (BDH), whereas zeolites with a larger number of acidic sites have been selected for targeting aromatization reactions. Methods for preparing these zeolite supports are for example disclosed in Bjørgen et al. (2008), Methanol to gasoline over zeolite H-ZSM-5: Improved catalyst performance by treatment with NaOH. *Applied Catalysis A: General* 345, 43-50.

The nanoparticles in the catalyst composition are well-distributed all through the porous support surface. In a particular embodiment, the support displayed porous size in the mesoporous range from 1 nm to 50 nm. In a particular embodiment, the support displayed porous size in the microporous range around 1 nm.

In another also particular embodiment of the catalyst compositions of the first aspect, the percentage by weight of the one or more of the metallic element of group 10 is from 0.2 to 5.0%, more in particular it is from 0.2 to 2.5%, or even more in particular it is from 0.2 to 2.0%, and the percentage by weight of the one or more organic molecule selected from the group consisting of an organophosphorus compound, and an N-heterocyclic carbene is from 0.05 to 0.2%, being all percentages in relation with the total weight of catalyst composition, thus, in relation to the total weight of the catalyst composition comprising the metallic nanoparticle and the porous support, the cocatalysts and optionally the promoters if they are present.

In a more particular embodiment, the percentage by weight of the one or more element of group 10, in relation with the total weight of the catalyst composition, is from 0.5 wt % to 2.5 wt %, more in particular from 1.0 wt % to 2.5 wt % including 1.0, 1.5, 2.0 and 2.5 wt %.

When in this description the term "wt %" or "w/w" or "percentage by weight" is indicated, it refers to the amount of the single component relative to the total weight of the composition or, if specifically mentioned, of other component. For example, Pt 1 wt % relates to 1 wt % of platinum in the final catalyst composition. When the catalyst composition comprises two or more of the platinum (Pt), nickel (Ni) and palladium (Pd), the above indicated percentages by weight correspond either to the percentage of each of the elements or to the sum of the elements.

As above indicated, the catalyst composition comprises tin (Sn), gallium (Ga), indium (In) and combinations thereof. In a more particular embodiment, the one or more metallic elements selected from the group consisting of Sn, Ga, and In, are in a percentage by weight from 0.15 to 1.0% in relation with the total weight of the catalyst composition. In another particular embodiment, the catalyst composition comprises one or more catalyst promoters, in particular selected from lithium (Li), sodium (Na), and combinations, in a percentage by weight from 0.8 to 2.0%, all percentages in relation with the total weight of the catalyst composition. As before, when the catalyst composition comprises two or more of the Sn, Ga and In, as cocatalysts, or Li and Na as promoters, the above indicated percentages by weight correspond either to the percentage of each of the elements (e.g. Sn) or to the sum of the elements (e.g. Sn and Ga in a Pt/Ga_NP@support).

In also another particular embodiment of the first aspect, the catalyst composition comprises:
 (a) a metallic nanoparticle; and
 (b) a porous support with a surface area, wherein the nanoparticle (a) is adsorbed on the surface area of the porous support;
 wherein the nanoparticle (a) comprises: (i) a percentage by weight from 0.2 to 5.0% of one or more metallic elements of group 10 of the periodic table; (ii) a percentage by weight from 0.05 to 0.2% of one or more organic molecules selected from the group consisting of an organophosphorus compound, and an N-heterocyclic carbene; and (iii) a percentage by weight from 0.15 to 1.0% of one or more metallic elements selected from the group consisting of Sn, Ga, and In, all percentages in relation with the total weight of catalyst composition; and
 wherein the porous support (b) comprises a percentage by weight from 0.8 to 2.0% of one or more catalyst promoters, such as Li and/or Na, said percentages also in relation with the total weight of catalyst composition.

Further, in another more particular embodiment of the catalyst composition of the first aspect, optionally in combination with any of the embodiments of the composition above or below, it comprises:
 (a) a metallic nanoparticle; and
 (b) a porous support with a surface area; wherein the nanoparticle (a) is adsorbed on the surface area of the porous support;
 the said nanoparticle (a) comprising: (i) one or more metallic elements of group 10 of the periodic table selected from platinum (Pt) and nickel (Ni); (ii) one or more organic molecules selected from the group consisting of an organophosphorus compound, and an N-heterocyclic carbene; and (iii) one or more metallic elements selected from the group consisting of tin (Sn), gallium (Ga).

In also another particular embodiment of the catalyst composition, the nanoparticle is a multimetallic nanoparticle that comprises, or consists of, group 10 atoms, in particular atoms of Ni and/or Pt, and optionally Pd and; atoms of Sn, Ga, In, and combinations thereof, as cocatalysts; the nanoparticle being stabilized with organophosphorus compounds (i.e. P-coordinating compounds), such as phosphines. Particular phosphines include $PPh_3$.

In a particular embodiment of this first aspect, optionally in combination with any embodiment of the compositions above or below, the nanoparticle includes Pt as the only element of group 10 and $PPh_3$ as organic stabilizing agent (i.e. a particular example of organophosphorus compound), and it further comprises one or more elements selected from the group consisting of Sn, Ga, and In.

In also another particular embodiment of the catalyst composition, the nanoparticle is a bimetallic or bielement nanoparticle that comprises or consists of, group 10 atoms, in particular atoms of Ni or Pt, and atoms of one of Sn, Ga and In (i.e. the cocatalysts), the said bimetallic nanoparticle stabilized with organophosphorus compounds (i.e. P-coordinating compounds), such as phosphines, more in particular $PPh_3$. In a more particular embodiment, the bimetallic nanoparticle comprises Pt atoms and Sn atoms and the organophophorus compound as the organic stabilizing agent.

In another particular embodiment of this catalyst composition with bimetallic nanoparticles, the said catalyst composition further comprises one or more cocatalyst atoms of Sn, Ga and In, adsorbed onto the surface area of the selected porous support. In yet another more particular embodiment, the wt % of Pt in the total catalyst is ranging from 1.0 to 2.0 wt % and the wt % of Sn in the total catalyst (in the nanoparticle and adsorbed on the support) is from 0.2 to 0.7 wt %. In yet another more particular embodiment, the wt % of Pt in the total catalyst is ranging from 1.0 to 2.0 wt % and the wt % of Ga in the total catalyst (in the nanoparticle and adsorbed on the support) is from 0.2 to 0.7 wt %. In yet another more particular embodiment, the wt % of Pt in the total catalyst is ranging from 1.0 to 2.0 wt % and the wt % of In in the total catalyst (in the nanoparticle and adsorbed on the support) is 0.2 to 0.7 wt %. In yet another more particular embodiment of the catalyst composition with at least bimetallic nanoparticles, the wt % of Ni in the total catalyst is ranging from 1.0 to 2.0 wt % and the wt % of Sn in the total catalyst (in the nanoparticle and adsorbed on the support) is from 0.2 to 0.7 wt %.

In another particular embodiment of the catalyst composition, it comprises trimetallic nanoparticles. In a more particular embodiment the trimetallic nanoparticles comprise Pt, Ni and Sn. In a more particular embodiment of this catalyst composition with trimetallic nanoparticles, the wt % of Ni and Pt in the total catalyst is ranging from 1.0 to 2.0 wt % and the wt % of Sn in the total catalyst (in the nanoparticle and adsorbed on the support) is from 0.2 to 0.7 wt %.

Particular combinations of metals in the nanoparticles with several mesoporous supports, as previously disclosed, are illustrated in examples below.

In this description also disclosed are some catalyst compositions with monometallic nanoparticles adsorbed on porous supports (all along the surface area). In particular, the nanoparticle is a metal nanoparticle that comprises only platinum (Pt) atoms and organophosphorus compounds (i.e., P-coordinating compounds), such as phosphines, more in particular $PPh_3$. In another more particular embodiment of this monometallic nanoparticle containing catalyst the wt % of Pt in the total catalyst is then from 1.0 wt % to 5.0 wt %.

Another aspect of the invention is a process for the preparation of a catalyst composition as defined in the first aspect, comprising in a one-pot step, the decomposition of one or more organometallic precursor compounds of one or more elements of group 10, and of one or more organometallic precursors compounds of one or more metallic elements selected from the group consisting of tin (Sn), gallium (Ga), and indium (In), in the presence of an organic solvent, a porous support, and of one or more organic molecules selected from the group consisting of an organophosphorus compound and an N-heterocyclic carbene; the one-pot decomposition carried out at a temperature from 20° C. (r.t) to 100° C. for a period from 30 minutes to 70 hours, and at a pressure from $1.0 \times 10^5$ Pa to $5.0 \times 10^5$ Pa in hydrogen gas atmosphere.

If the catalyst composition must contain catalyst promoters, in particular selected from Li and Na, these elements are added to the reaction mixture, or they are provided with the porous support by reacting the supports with alkaline bases (i.e., sodium hydroxyde (NaOH) for zeolites, or organometallic lithium reagents (for alumina)). (See Bjørgen et al. (2008) and Rouge et al. (2019), supra).

In a particular embodiment of the process of preparation, the one or more organometallic precursor compounds are added in an amount of 1 mole of group 10 atoms per 0.1 to 1.0 moles of the one or more organic molecules selected from the group consisting of an organophosphorus compound, and an N-heterocyclic carbene (i.e., the organic nanofabrication controlling agents).

Thus, the initial ratio of organic nanofabrication agent (i.e. organic ligands or organic stabilizing agents) in the nanoparticle preparation is 0.1-1.0 mole per mole of metal of group 10, and the final ratio of organic nanofabrication agent in the isolated nanoparticle in the catalyst (i.e. in the nanocatalyst composition) depends on the nanofabrication agent varying between 0.1-1.0 moles per mole of metal of group 10.

In yet another particular embodiment of the process according to the second aspect, the organometallic precursor compounds are selected from the group consisting of bis- and tris(dibenzylideneacetone) of metallic elements of Group 10, 1,5-cyclooctadienedimethyl of metallic elements of Group 10, ($C_1$-$C_4$)-alkyl complexes of the cocatalyst elements Sn, Ga, and In, and combinations of all these organometallic precursors. In a more particular embodiment, the organometallic precursor compounds are selected from tris(dibenzylideneacetone) platinum (abbreviated $Pt_2$($dba$)$_3$), 1,5-cyclooctadienedimethylplatinum (abbreviated $Pt^{(II)}$ (COD)$Me_2$), biscyclooctadienenickel (abbreviated $Ni^{(0)}$ (COD)$_2$), tetrabutyl tin (abbreviated $Sn^{(IV)}$ $Bu_4$), tetramethyl tin (abbreviated $Sn^{(IV)}$ $Me_4$), tributyltin hydryde (abbreviated $HSn^{(IV)}$ $Bu_3$), hexabutyl tin (abbreviated $Sn_2^{(II)}$ $Bu_6$), hexamethyl tin (abbreviated $Sn_2^{(III)}$ $Me_6$), N,N'-Di-t-butyl-2,3-diamidobutane tin (abbreviated $Sn^{(II)}$ $C_{12}H_{26}N_2$), trimethyl gallium (abbreviated $GaMe_3$), and cyclopentadienyl indium (abbreviated InCp).

In another particular embodiment of the process of preparation, optionally in combination with any of the method embodiments above or below, the organic solvent is selected from the group consisting of ether containing solvents (in particular tetrahydrofuran, methyl-tetrahydrofuran, dioxane and diethyl ether), aromatic solvents (in particular benzene, toluene, anisole, methyl anisole and xylenes) and alkanes (in particular cyclohexane, hexane, pentane) and mixtures thereof.

In another particular embodiment of the process of preparation, optionally in combination with any of the method embodiments above or below, the organophosphorus compound is a compound of formula (I), as defined for the first aspect of the invention and its corresponding embodiments. Thus, the process is in particular carried out with an organophosphorus compound of formula (I) selected from phosphites and phosphines, the later including oxidized posphines and phosphoramidites. In particular, the organophosphorus compound for carrying out the process is selected from the group consisting of triphenylphosphine, 1,2-bis(diphenylphosphino)methane, tris(dimethylamino) phosphine, diphenylphosphine oxide, and trioctylphosphine oxide, triphenylphosphite, and combinations thereof.

The process of preparation of the catalyst is carried out, in a particular embodiment, at a room temperature, from 20° C. to 35° C., and at a pressure from $2.0 \times 10^5$ Pa to $4.0 \times 10^5$ Pa in hydrogen gas atmosphere. More in particular, it is carried out at room temperature and at a pressure of $3.0 \times 10^5$ Pa in hydrogen gas atmosphere. Hydrogen gas allows a reductive environment that, as will be depicted below, starts reducing the organometallic compounds to obtain the metals that will conform the nanoparticles and/or will be deposited onto the surface of the selected support.

On the alternative, the process of preparation of the catalyst is carried out, in a particular embodiment, at a temperature from 90° C. to 100° C., and at a pressure from $2.0 \times 10^5$ Pa to $4.0 \times 10^5$ Pa in hydrogen gas atmosphere. More in particular, it is carried out at 100° C. and at a pressure of $3.0 \times 10^5$ Pa in hydrogen gas atmosphere.

As previously indicated, in a particular embodiment, the catalyst composition may also be defined by the process of preparation of the second aspect. All particular embodiments of this second aspect apply then to the said catalyst composition obtainable by it.

Thus, the invention also encompasses a catalyst composition comprising:
(a) a metallic nanoparticle; and
(b) a porous support with a surface area; wherein the nanoparticle (a) is adsorbed on the surface area of the porous support;
wherein the nanoparticle (a) comprises (i) one or more metallic elements of group 10 of the periodic table; (ii) one or more organic molecules selected from the group consisting of an organophosphorus compound, and an N-heterocyclic carbene; and (iii) one or more metallic elements selected from the group consisting of tin (Sn), gallium (Ga), and indium (In);
said catalyst composition obtainable by the decomposition, in a one-pot step, of one or more organometallic precursor compounds of one or more elements of group 10, and of one or more organometallic precursors compounds of one or more metallic elements selected from the group consisting of tin (Sn), gallium (Ga), and indium (In), in the presence of an organic solvent, a porous support, and of one or more organic molecules selected from the group consisting of an organophosphorus compound and an N-heterocyclic carbene; the one-pot decomposition carried out at a temperature from 20° C. (r.t) to 100° C. for a period from 30 minutes to 70 hours, and at a pressure from $1.0 \times 10^5$ Pa to $5.0 \times 10^5$ Pa in hydrogen gas atmosphere.

One-pot synthesis of the catalyst compositions is highly advantageous as previously disclosed, since it is a simple, affordable and reliable method of preparing the highly effective and selective catalysts of the invention.

Nonetheless, an alternative mode of synthesis of the catalyst compositions departs from colloidal suspensions comprising the metallic nanoparticles as a suspended discrete phase in an organic solvent, as the continuous phase. These colloidal suspensions are then deposited on the porous supports by impregnation approach.

The method to support colloidal nanoparticles onto supports includes two steps. In the first step, in a Fisher Porter reactor, the desired organometallic precursor(s) (containing one or more metallic elements from the group of tin (Sn), gallium (Ga), indium (In), platinum (Pt) or palladium (Pd)) is/are placed in the presence of one or more organic molecules selected from the group consisting of an organophosphorus compound and an N-heterocyclic carbene (i.e., a nanofabrication controlling agent). The mixture is in the presence of an organic solvent and decomposed under hydrogen atmosphere (particular pressure from $1.0 \times 10^5$ Pa to $5.0 \times 10^5$ Pa) and heated at 20° C. (r.t) to 100° C. for a period from 30 minutes to 70 hours. After, the remaining hydrogen pressure is evacuated and the colloidal nanoparticle dispersion is maintained under inert atmosphere. In the second step, an impregnation procedure is followed, in which a determined volume of colloidal nanoparticle dispersion, depending on the metal % desired onto the support, is added by a cannula to a Schlenk flask with the selected support (e.g., $Al_2O_3$ and ZSM-5) and the mixture is exposed to ultrasound to favour the diffusion of the nanoparticles into the support pore system. The mixture is then stirred for a period from 1 to 7 days. The remaining mixture is filtered and washed with dry degassed hexane. The material is dried under vacuum and stored under inert atmosphere.

This alternative method implies two steps, but it is still affordable and of low complexity in relation with the processes for obtaining some of the commercial catalysts employed nowadays in the field of n-ODH. Moreover, an additional advantage of this method is that the support can be selected according to the desire of the final user.

Thus, the invention also includes a colloidal suspension catalyst composition comprising a metallic nanoparticle (a) suspended in an organic solvent (b), and wherein the nanoparticle (a) comprises (i) one or more metallic elements of group 10 of the periodic table; (ii) one or more organic molecules selected from the group consisting of an organophosphorus compound, and an N-heterocyclic carbene; and (iii) one or more metallic elements selected from the group consisting of tin (Sn), gallium (Ga), and indium (In).

These colloidal suspensions are, in particular, obtained by a method comprising the decomposition of one or more organometallic precursor compounds of one or more elements of group 10, and of one or more organometallic precursors compounds of one or more metallic elements selected from the group consisting of tin (Sn), gallium (Ga), and indium (In), in the presence of an organic solvent, and of one or more organic molecules selected from the group consisting of an organophosphorus compound and an N-heterocyclic carbene; the one-pot decomposition carried out at a temperature from 20° C. (r.t) to 100° C. for a period from 30 minutes to 70 hours, and at a pressure from $1.0 \times 10^5$ Pa to $5.0 \times 10^5$ Pa in hydrogen gas atmosphere.

Particular embodiments of the nanoparticles in the catalyst composition of the first aspect of the invention, regarding the combination of metallic elements of the group 10 of the periodic table, and of the one or more of Sn, Ga and In, or of the particular organic molecules selected from the group consisting of an organophosphorus compound, and an N-heterocyclic carbene, do also apply to these colloidal suspensions of the nanoparticles.

The organic solvent in these colloidal suspensions is, in a particular embodiment, selected from the group consisting of ether containing solvents (in particular tetrahydrofuran, methyl-tetrahydrofuran, dioxane and diethyl ether), aromatic solvents (in particular benzene, toluene, anisole, methyl anisole and xylenes) and alkanes (in particular cyclohexane, hexane, pentane) and mixtures thereof.

In the same way, particular organometallic precursor compounds and their initial and final mole ratios with the organic molecules disclosed in the process for preparing the catalyst composition of the first aspect, particular temperature ranges and times do also apply to the preparation of these colloidal suspensions that are also conceived as intermediate products to obtain the catalyst compositions of the first aspect.

The present invention also relates to a process for producing one or more ($C_2$-$C_4$)-alkenes, and/or one or more ($C_6$)-aromatic compounds, the process comprising a non-oxidative dehydrogenation of an ($C_2$-$C_4$)-alkane and/or of an ($C_3$-$C_4$)-alkene or, for the production of the one or more ($C_6$)-aromatic compounds, a non-oxidative dehydrogenation of an ($C_2$-$C_4$)-alkane and/or a non-oxidative dehydrogenation of a ($C_6$)-cycloalkane compound, said dehydrogenation carried out with a step of contacting a feed stream comprising the ($C_2$-$C_4$)-alkane and/or the ($C_3$-$C_4$)-alkene, or the ($C_2$-$C_4$)-alkane and/or the ($C_6$)-cycloalkane, with the catalyst composition as defined in the first aspect, to obtain the one or more alkenes and the one or more aromatic compounds.

In a particular embodiment of the process for producing one or more ($C_2$-$C_4$)-alkenes and/or one or more ($C_6$)-aromatic compounds, the alkenes are selected from ethylene, propylene and butadiene, and the one or more aromatic compounds are selected from benzene, toluene, orto-, meta-, para-xylene and mixtures thereof.

The term "non-oxidative dehydrogenation" is understood to mean that the dehydrogenation proceeds substantially in the absence of an oxidizing agent, such as oxygen or carbon dioxide, i.e. the amount of oxidizing agent in a feed stream comprising the alkane is at most 1 vol based on the feed stream.

Examples below illustrate that propane is highly converted to propene and in a very selective way (no other side-reactions) when catalysts of the invention (first aspect) are used. Thus, in a particular embodiment of the process for obtaining ($C_2$-$C_4$)-alkenes and/or ($C_6$)-aromatic compounds from alkanes and ($C_6$)-cycloalkanes, the alkane is propane and the alkene obtained is propylene.

In another particular embodiment of the process for obtaining ($C_2$-$C_4$)-alkenes of the third aspect, the nODH of the ($C_3$-$C_4$)-alkene being 2-butene (a $C_4$-alkene) is carried out to obtain butandiene (another more oxidized $C_4$-alkene).

In yet another particular embodiment of the process for obtaining ($C_2$-$C_4$)-alkenes, butandiene is obtained by nODH of a mixture comprising 2-butene (a $C_4$-alkene) and butane (a $C_4$-alkane).

In another particular embodiment of the process, the non-oxidative dehydrogenation is performed at a temperature of from 400 to 650° C. In another particular embodiment, it is performed at a temperature of from 500 to 600° C., including 500, 510, 520, 530, 540, 550, 560, 570, 580, 590 and 600° C.

In another particular embodiment of the process, the non-oxidative dehydrogenation is performed at a feed stream flow comprising from 1.5 mL/min to 3.0 mL/min of the ($C_2$-$C_4$)-alkane and/or ($C_6$)-aromatic compounds, in a particular example, it is performed at 3.0 mL/min of a feed stream flow comprising or consisting in ($C_2$-$C_4$)-alkane, more in particular, propane.

In another particular embodiment of the process, the non-oxidative dehydrogenation is performed in the presence of an inert gas, which is, in particular applied at a flow from 10.5 to 21 mL/min. In a particular embodiment the inert gas is selected from argon (Ar) and nitrogen ($N_2$). In a more particular embodiment, the gas is Ar and its flow in the feed stream is 21 mL/min.

In another particular embodiment of the process, the non-oxidative dehydrogenation is performed in the presence of hydrogen gas at a flow from 0 to 3.0 mL/min. In a more particular embodiment, the flow of hydrogen is from 0.1 to 3.0 mL/min. In another more particular embodiment, the flow of hydrogen is from 0 to 1.5 ml/min. These flows of hydrogen provide 0 to 0.5 mole of hydrogen per mole of ($C_2$-$C_4$)-alkane and/or ($C_6$)-aromatic compounds.

In another particular embodiment of the process, the non-oxidative dehydrogenation is performed at a pressure from $5.0 \times 10^4$ Pa to $1.5 \times 10^5$ Pa, in a particular embodiment, $1.0 \times 10^5$ Pa (1 bar).

In also another more particular embodiment of the process of the third aspect, the non-oxidative dehydrogenation is performed at a temperature of from 400 to 650° C., a feed stream flow that comprises from 0.1 mL/min to 3.0 mL/min of the ($C_2$-$C_4$)-alkane, in a particular example 3.0 mL/min of propane; from 10.5 to 21 mL/min of an inert gas, in a particular example 21 mL/min of argon (Ar); and from 0 to 1.5 mL/min of hydrogen, in a particular example 0.5 mL/min hydrogen; and the non-oxidative dehydrogenation is carried out at a pressure from $5.0 \times 10^4$ Pa to $1.5 \times 10^5$ Pa, in a particular embodiment, $1.0 \times 10^5$ Pa (1 bar).

In a more particular example of the process, it is performed at a temperature of 530° C., with a feed stream flow of 3 mL/min of the ($C_2$-$C_4$)-alkane, in particular propane, 21 mL/min of argon and 1 mL/min of hydrogen, and at a pressure of 1 bar ($1 \times 10^5$ Pa).

Inventors have also realized that even a better performance and yield of the process for producing alkenes and/or aromatic compounds is achieved if it further comprises a step of catalyst pre-treatment. In another particular embodiment of the process, it further comprises a catalyst pre-treatment comprising submitting the catalyst composition under a hydrogen gas flow of 10 to 20 mL/min for a period of time from 4 to 16 hours, while increasing the temperature from 20° C. to 500° C.-600° C. at a rate of 1° C./min.

In another embodiment, the non-oxidative dehydrogenation is performed in the presence of a poisoning molecule.

Finally, in also another particular embodiment of the process for producing one or more ($C_2$-$C_4$)-alkenes and/or one or more ($C_6$)-aromatic compounds of the third aspect, the amount of catalyst composition is from 20 to 200 mg per total volume of feed stream. These amounts of catalyst compositions result in highly selective (selectivity higher than 99%) transformation of propane feeds with much higher conversion rates (23-25% at 530° C. and 1 bar) and stabilities than the conventional catalysts. (see examples below).

Thus, in a particular example the new catalyst compositions are applicable in a process for the non-oxidative catalytic dehydrogenation of propane, which process comprises the step of passing the feed to be dehydrogenated onto the catalyst (i.e. catalyst composition), said catalyst containing from 0.2 to 5.0%, in particular 0.2 to 2.0% by weight of group 10 element (nickel, palladium and platinum, and combination thereof), said group 10 element(s) in nanoparticles, from 0.05 to 0.2% by weight of organic molecule as nanofabrication controlling agent (N-coordinating compounds such as amines, P-coordinating compounds such as phosphines, C-coordinating N-heterocyclic carbenes, and combination thereof) also conforming the nanoparticles, the catalyst also containing from 0.15 to 1.0% by weight of cocatalyst (tin, gallium and indium, and combination thereof), from 0.8 to 2% by weight of alkaline (lithium and sodium) element as promoter, and said catalyst being obtained in one-pot by controlled decomposition in solution under hydrogen atmosphere ($1.0 \times 10^5$ Pa to $5.0 \times 10^5$ Pa) and temperature (25– to –100° C.) of catalyst and cocatalyst organometallic precursors in presence of the organic molecule (i.e. the nanofabrication controlling agent) and the mesoporous support. The dehydrogenation is carried out by a sequence of prereduction in the presence of hydrogen at a temperature comprised between 45° and 550° C., and a dehydrogenation of alkanes at a temperature comprised between 530° C. and 650° C., and at a pressure comprised between $5.0 \times 10^4$ Pa to $3.0 \times 10^5$ Pa, and a gas flow hourly space velocity (GHSV) comprised between 200 to 120 000 mL total flow×gcat$^{-1}$×h$^{-1}$ (2-to-14400 mL Propane×gcat$^{-1}$×h$^{-1}$).

Disclosed herewith are also catalyst compositions that are defined by as comprising:
(a) a metallic nanoparticle; and
(b) a porous support with a surface area; wherein the nanoparticle (a) is adsorbed on the surface area of the porous support;
wherein the nanoparticle (a) comprises (i) one or more metallic elements of group 10 of the periodic table; and (ii) one or more organic molecules selected from the group consisting of an organophosphorus compound, and an N-heterocyclic carbene, wherein at least one of the elements of group 10 in the nanoparticle is platinum (Pt) or nickel (Ni), and wherein when the nanoparticle comprises Ni as only element of group 10, it further comprises tin (Sn) and/or gallium (Ga), and when the nanoparticle comprises Pt as only element of group 10 the mole ratio of the one or more organic molecules and the one or more metallic elements of group 10 is of 0.05-0.25:1.

Also a process for preparing a catalyst composition as defined in the paragraph above, comprising in a one-pot step, the decomposition of one or more organometallic precursor compounds of one or more elements of group 10, one of the organometallic precursor compounds comprising platinum and/or nickel, in the presence of an organic solvent, a porous support, and of one or more organic molecules selected from the group consisting of an organophosphorus compound and an N-heterocyclic carbene; the one-pot decomposition carried out at a temperature from 20° C. (r.t) to 100° C. for a period from 30 minutes to 70 hours, and at a pressure from $1.0 \times 10^5$ Pa to $5.0 \times 10^5$ Pa in hydrogen gas atmosphere; and wherein when the catalyst composition comprises nanoparticles comprising nickel as only element of the group 10, then one or more of the organometallic precursor compounds comprise tin and/or gallium; and when the catalyst composition comprises platinum as the only element of the group 10, the mole ratio in the reaction of Pt and of the one or more of the organic molecules is that giving a final mole ratio of organic molecule and Pt of 0.05-0.25:1.

Also part of the present invention is, thus, a catalyst composition comprising:
(a) a metallic nanoparticle; and
(b) a porous support with a surface area; wherein the nanoparticle (a) is adsorbed on the surface area of the mesoporous support;
wherein the nanoparticle (a) comprises (i) one or more metallic elements of group 10 of the periodic table; and (ii) one or more organic molecules selected from the group consisting of an organophosphorus compound, and an N-heterocyclic carbene, wherein at least one of the elements in the nanoparticle is platinum (Pt) and/or nickel (Ni), and wherein if the nanoparticle comprises Ni as only element of group 10 it also comprises tin (Sn) and/or gallium (Ga), and when the nanoparticle comprises Pt as only element of group 10 the mole ratio of the one or more organic molecules and the one or more metallic elements of group 10 is of 0.05-0.25:1;
said catalyst composition obtainable by the decomposition, in a one-pot step, of one or more organometallic precursor compounds of one or more elements of group 10, one of the organometallic precursor compounds comprising platinum (Pt) and/or nickel (Ni), in the presence of an organic solvent, a mesoporous support, and of one or more organic molecules selected from the group consisting of an organophosphorus compound, and an N-heterocyclic carbene; the one-pot step decomposition carried out at a temperature from 20° C. (r.t) to 100° C. for a period from 30 minutes to 70 hours, and at a pressure from $1.0 \times 10^5$ Pa to $5.0 \times 10^5$ Pa in hydrogen gas atmosphere; and wherein when the catalyst composition comprises nanoparticles comprising nickel as the only element of group 10, then one or more of the organometallic precursor compounds comprise tin (Sn) and/or gallium (Ga); and wherein when the catalyst composition comprises nanoparticles comprising platinum as the only element of group 10, the mole ratio in the reaction of Pt and of the one or more of the organic molecules is that giving a final mole ratio of organic molecule and Pt of 0.05-0.25:1.

Also herewith disclosed is a process for preparing a catalyst composition, said catalyst comprising
a) a metallic nanoparticle that comprises one or more metallic elements of group 10 of the periodic table and one or more metallic elements selected from the group consisting of tin (Sn), gallium (Ga), and indium (In); and
(b) a porous support with a surface area; wherein the nanoparticle (a) is adsorbed on the surface area of the porous support;
the process comprising in a one-pot step, the decomposition of one or more organometallic precursor compounds of one or more elements of group 10, and the decomposition of one or more organometallic precursors compounds of one or more metallic elements selected from the group consisting of tin (Sn), gallium (Ga), and indium (In), in the presence of an organic solvent and a porous support; the one-pot decomposition carried out at a temperature from 20° C. (r.t) to 100° C. for a period from 30 minutes to 70 hours, and at a pressure from $1.0 \times 10^5$ Pa to $5.0 \times 10^5$ Pa in hydrogen gas atmosphere.

As will be illustrated in the Examples below, the process of previous paragraph allowed obtaining nanoparticles of PtSn with a mean diameter of 1.42 nm. The Pt content in the catalyst composition was of 1.328 wt % (in relation to the total weight of the catalyst composition and measured by ICP). The Sn content was of 1.381 wt % (in relation to the total weight of the catalyst composition and measured by ICP). The molar ratio of Pt and Sn was of 1.71.

Thus, in a particular example of this process, the element of group 10 is Pt. In another particular example, the metallic element is tin (Sn). In even a more particular example, the element of group 10 is Pt and the element is tin (Sn).

This process supposes an advantage process in relation to others used for obtaining these catalysts with nanoparticles of one or more elements of group 10, and with one or more metallic elements selected from the group consisting of tin (Sn), gallium (Ga), and indium (In), since the process implies lower costs in terms of using lower temperatures and times of prosecution. All this at the same time, the obtained catalyst compositions include nanoparticles of very low mean diameter, making them very useful in the nODH reaction.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples are provided by way of illustration, and they are not intended to be limiting of the present invention. Furthermore, the present invention covers all possible combinations of particular and preferred embodiments described herein.

EXAMPLES

Example 1.—Preparation of Monometallic Nanocatalyst as Preliminary Test Products Concerning the preparation of monometallic Pt-nanocatalysts by organometallic approach, the synthesis of monometallic colloidal and supported Pt nanoparticles (Pt-NPs) was extensively studied. For instance, regarding the Pt-colloidal systems, the decomposition of the $Pt_2(dba)_3$ organometallic precursor was reported using various types of stabilizers (organic molecules as nanofabrication controlling agent) such as polymers (Pt1 with polyvinylpyrrolidone) and ligands (Pt2 and Pt3 with N- and P-ligands). Depending on the gas, solvent nature, stabilizer/metal ratio, reactants concentration and temperature, various shaped Pt nanostructures such as isolated small Pt-NPs, dendrites or crystalline nanowires were obtained.

Figure 2:
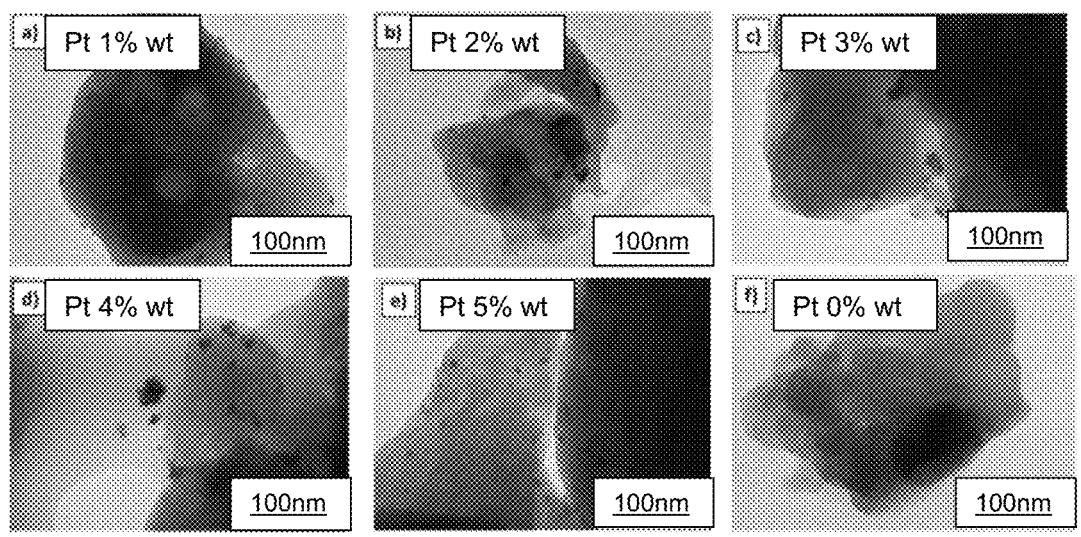
FIG. 2 shows TEM images of Pt-NPs stabilized with NHC—$CO_2$ supported on meso NaZSM5. Pt5a-5e (Pt (wt %): a) 1, b) 2, c) 3, d) 4, e) 5) and the TEM image of the support Na-ZSM5 (5f). Size-reference 100 nm.

The effect of the organic stabilizing agent was first evaluated through the preparation of some colloidal Pt-NPs, obtained by decomposition of $Pt_2(dba)_3$ in THF under 3 bar $H_2$ atmosphere at r.t. and stabilized by various organic molecules: none (FIG. 1, Pt4c THF), triphenylphosphine ($PPh_3$, FIG. 1, Pt4e), and 1,3-dimethyimidazolium carboxylate (NHC—$CO_2$, FIG. 2, Pt4f)). The decomposition of the Pt-precursor was quantitative obtaining in all cases small Pt-NPs. Analysis of TEM images, revealed 2-3 nm Pt-NPs for these samples.

Effect of the Metal Loading onto Supports:

Catalyst compositions were then produced using first 2 mesoporous zeolites NaZSM5 and HZSM5. Methods to obtain zeolites are known by the skilled person (see for example Bjørgen et al. (2008), cited above). The syntheses were performed in THF, although in toluene perform equally. The organometallic approach was followed, and NHC—$CO_2$ was used now as stabilizing agent (i.e., as source of carbene). Firstly, the effect of the metal loading was evaluated using NaZSM5. Five catalysts with different nominal metal loadings (Pt5a-Pt5e 1, 2, 3, 4 and 5 wt %) were prepared through in-situ decomposition of the $Pt_2(dba)_3$ under 3 bar $H_2$ atmosphere at r.t. in the presence of NHC—$CO_2$. TEM analyses revealed that small (3-4 nm) nanoparticles were formed in all cases (FIG. 2). 1 wt % revealed the optimal metal loading with uniform Pt-NPs distribution and no aggregates. HZSM5 was also evaluated using this methodology. Other catalyst compositions were then prepared with alumina-based supports ($Al_2O_3$, Li—$Al_2O_3$). Li—$Al_2O_3$ supports can be prepared as known by the skilled person in the art. Briefly, a solution of a lithium organometallic compound (e.g., n-butyl lithium in a polar solvent (e.g. cyclohexane) is added to $Al_2O_{3\text{-}500}$, after stirring the suspension overnight at room temperature, the solvent is washed (see Rouge et al. (2019), cited above). Pt-NPs supported onto these alumina supports with loadings of 1 and 2 wt % displayed smaller Pt-NPs (1-2 nm) than those in NaZSM5.

Effect of the $PPh_3$ in the Bimetallic Supported Catalysts Using Toluene:

Although bimetallic catalysts are disclosed in more detail in Example 2 below, here is also disclosed an example with $PPh_3$ as organic stabilizing agent and toluene as solvent. Pt 2 wt. %-Sn 1 wt. % and four supports $Al_2O_3$ ($Pt_6c$), Li—$Al_2O_3$ ($Pt_7c$), Na-ZSM5 ($Pt_8c$) and H-ZSM5 (Pt9c), were used. The use of $PPh_3$ as ligand resulted in the formation of small PtSn-NPs onto the four supports (i.e., 1-2 nm).

Surface area measurements (i.e., BET (Brunauer, Emmet, and Teller) isotherm, pore size and pore distribution) of the bare supports, 1 wt. % Pt (prepared with $PPh_3$ as organic stabilizing agent and toluene as solvent, as comparative) onto $Al_2O_3$ (Pt6a), Li—$Al_2O_3$ (Pt7a), Na-ZSM5 (Pt8a) and H-ZSM5 (Pt9a), 2 wt. % Pt (prepared with $PPh_3$ as organic stabilizing agent and toluene as solvent, as comparative) onto $Al_2O_3$ (Pt6b), Li—$Al_2O_3$ (Pt7b), Na-ZSM5 (Pt8b) and H-ZSM5 (Pt9b), and 2 wt. % Pt—Sn 1 wt % stabilized with $PPh_3$ onto $Al_2O_3$ (Pt6c), Li(0.46%)-$Al_2O_3$ (Pt7c), Na-ZSM5 (Pt8c) and H-ZSM5 (Pt9c); were measured using a Micrometrics ASAP 2020 Physisorption instrument. Surface Area is a measure of the exposed surface of a solid sample on the molecular scale. The BET theory is the most popular model used to determine the area. During processing, especially in particle size reduction, the specific surface area of the product can change. Any subsequent change during the manufacturing process may affect the porosity and surface area. These changes can lead to an unexpected change in desired performance. Samples are commonly prepared by heating while simultaneously evacuating or flowing gas over the sample to remove the impurities. The prepared samples are then cooled with liquid nitrogen and analyzed by measuring the volume of gas adsorbed at specific pressures. Thus, the above samples were pre-treated at 250° C. for 4 h under vacuum. The results regarding the alumina's support are showed in Table 1. The difference of the area (i.e., 125±9 $m^2$/g) and pore volume (0.65±0.06 $cm^3$/g) values of the samples without and with NPs displayed are not significant and they were attributed to small different efficiency of the individual sample pre-treatment (i.e., sample weighting process precision, real vacuum and temperature achieved in the pre-treatment, etc). This means that there is a partial filling of the support pores without blocking them, and then, the catalytic performance of these materials can be compared. Similar tendency was observed with Na-ZSM5, H-ZSM5 and Li—$Al_2O_3$.

TABLE 1

BET results for alumina supported catalysts.

| Sample | BET ($m^2$/g) | Total pore volume ($cm^3$/g) |
| --- | --- | --- |
| $Al_2O_3$ support | 116 | 0.69 |
| Pt6a Pt(1%)-$PPh_3$@$Al_2O_3$ | 134 | 0.71 |
| Pt6b Pt(2%)-$PPh_3$@$Al_2O_3$ | 113 | 0.60 |
| Pt6c Pt(2%)/Sn(1%)-$PPh_3$@$Al_2O_3$ | 126 | 0.71 |

Example 2-Preparation of Nanocatalysts of PtSn with Sn(III and IV) Precursors (Catalysts Compositions According to the Invention)

Figure 3:
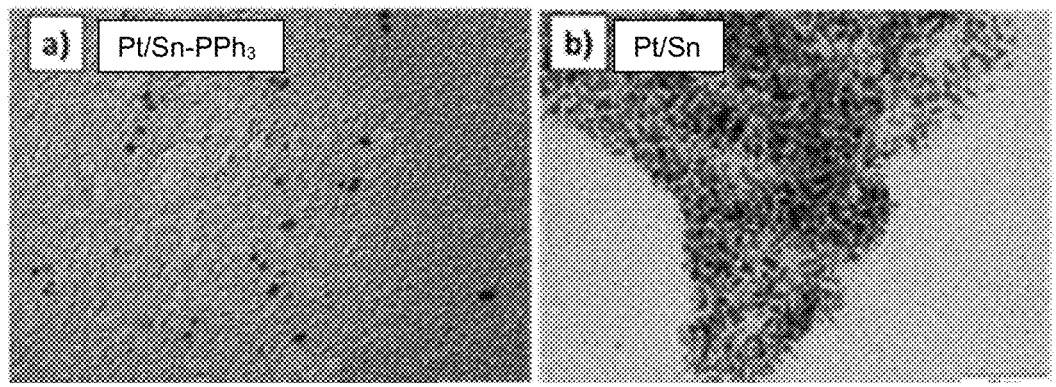
FIG. 3 includes TEM images of PtSn-NPs (Pt10 and Pt11) with $PPh_3$ (a) and no stabilizing agent (b).

2.1. Assay of the Organic Stabilizing Agent in PtSn Colloidal NPs with Sn(III and IV) Precursors Bimetallic PtSn-NPs (Pt10) were prepared using $Pt_2(dba)_3$ and $SnBu_4$ as organometallic precursors in a Pt/Sn molar ratio 1:1, in the presence of $PPh_3$ as a possible phosphine, although all phosphines are useful, and using toluene at r.t under 3 bar of $H_2$. Pt10 displayed small and well-dispersed NPs size of 2.0-2.3 nm by TEM (FIG. 3 (*a*)). These values are in agreement with those provided by XRD (crystallite sizes of 1.25±0.06 nm (data not shown). Bimetallic PtSn NPs (Pt11) were also obtained without $PPh_3$ (FIG. 3 (*b*)), however the formation of aggregates was observed, thus showing the positive effect of the phosphines (i.e., $PPh_3$) stabilizing agent. These results thus provided evidence of the importance of the organic stabilizing agent for the one-step preparation of PtSn-NPs by the organometallic approach. $^{31}P$ NMR analyses of the washing solutions showed no phosphorous-signal suggesting that the phosphorus-compounds remained in the catalyst surfaces.

Then, different metallic precursors and combinations of them were also assayed. The decomposition of the Pt and Sn precursors at 100° C. was monitored by GC-TCD quantification of some products resulting from the complex decomposition (i.e., methane and butane) in aliquots from reaction mixture collected at regular time intervals. The metallic precursors were: for Pt, $Pt^{(0)}_2(dba)_3$ and $Pt^{(II)}(COD)(Me)_2$, and for Sn(III) and Sn(IV) precursors, such as, $SnBu_4$, $HSnBu_3$, $SnMe_4$ and $Sn_2Bu_6$. See formulas below, where other organometallic precursors useful for the preparation of the catalysts compositions of the invention are also listed:

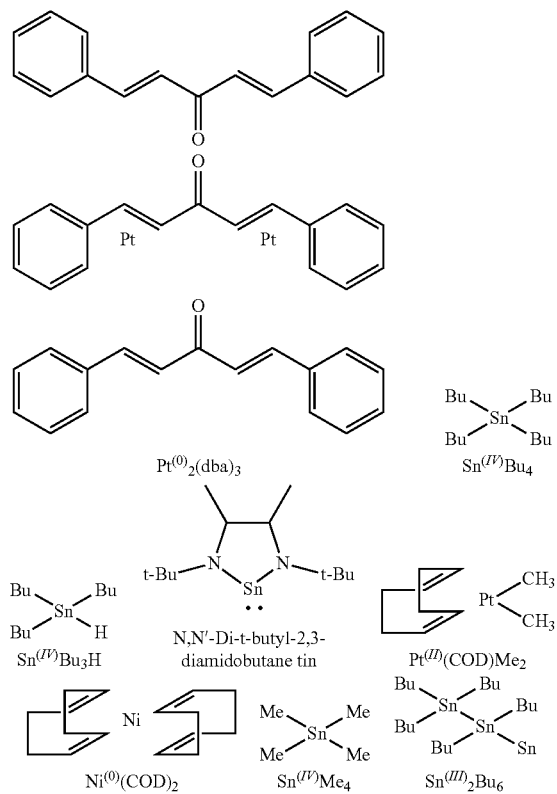

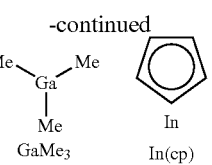

The results showed that in presence of $SnBu_4$, the Pt precursor (either $Pt^{(0)}_2(dba)_3$ (Pt12) or $Pt^{(II)}(COD)(Me)_2$ (Pt13)) decomposes quantitatively over a period of time of <15-20 h and the $SnBu_4$ partially decomposes (2-4% for (Pt12) and 7-10% for ($Pt_{13}$)) over a period of time of >40 h.

In presence of $Pt^{(II)}(COD)(Me)_2$ and over period of time of >40 h, the Sn(III) and Sn(IV) precursors decomposes at a extend of less than 15%, for example, the $SnBu_4$ decomposes 5-10% (Pt13) and $HSnBu_3$ (Pt14) descomposes 10-to-15%. Similar behavior was observed for $SnMe_4$ (Pt15) and $Sn_2Bu_6$ (Pt16).

2.2. Supported Bimetallic Pt—Sn—NPs with Sn(III and IV) Precursors

Figure 4:
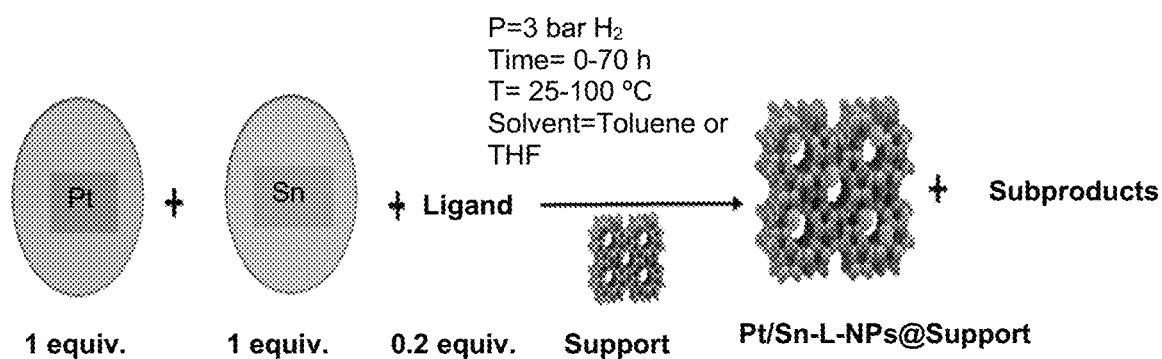
FIG. 4 schematically illustrates the one-pot organometallic synthesis for PtSn-L-NPs@Supports. L stands for Ligand, which represents the organic stabilizing agent.
Figure 5:
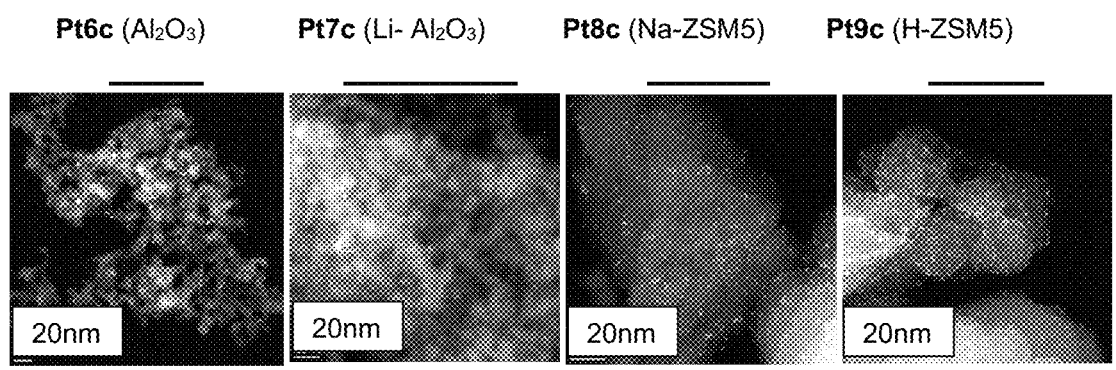
FIG. 5 includes High-resolution transmission electron microscopy (HRTEM) images of Pt 2% wt-Sn 1% wt. (Pt/Sn molar ratio is 1:1) Pt6c ($Al_2O_3$), Pt7c (Li—$Al_2O_3$), Pt8c (Na-ZSM5) and Pt9c (H-ZSM5). Size-reference 20 nm.

The decomposition of the Pt(0 and II) and Sn(III and IV) precursors onto the four supports $Al_2O_3$, Li—$Al_2O_3$, Na-ZSM5 and H-ZSM5 was carried out. The syntheses of supported bimetallic NPs is summarized in FIG. 4. The decomposition was carried out at 100° C. using $Pt_2(dba)_3$ and $SnBu_4$ as organometallic precursor and phosphines (i.e., $PPh_3$) as organic stabilizing agent (Ligand in FIG. 4). These samples presented a nominal metal loading of Pt 2% wt-Sn 1% wt. (Pt/Sn molar ratio is 1:1) and they were labeled Pt6c ($Al_2O_3$), Pt7c (Li—$Al_2O_3$), Pt8c (Na-ZSM5) and Pt9c (H-ZSM5). The decomposition of the Pt and Sn precursors was monitored by measuring the Pt and Sn content by inductively coupled plasma Optical Emission Spectroscopy (ICP-OES), Gas Chromatography with Thermal Conductivity detector (GC-TCD) analysis of the products in the gas phase generated by decomposition of the precursors and SEM-EDX, the nanoparticle mean diameter and dispersion measured by HAADF-STEM (see FIG. 5) and the crystalline phase was studied by XRD.

The results obtained revealed that (data not shown): (a) Pt-precursor was quantitatively decomposed forming small Pt-NPs and the decomposition rate was not affected by the nature of the support; (b) Sn-precursor was partially decomposed and the decomposition rate varied depending on nature of the support in the following order $Al_2O_3$ (Pt6c) >>Li—$Al_2O_3$ (Pt7c)=Na-ZSM-5 (Pt8c)>>H-ZSM-5 (Pt9c) >>>no support (behavior attributed to the presence of proton with amphoteric character in the alumina surface, i.e., Al—OH groups); and (c) the Sn(III and IV) precursors (for example, $SnBu_4$) in the presence of $Al_2O_3$ decomposed quite fast (70-to-100% after 40 h). The higher reactivity of the $Al_2O_3$ compared with the H-ZSM-5 could be related with the larger es and the easy access of the $SnBu_4$ precursors to the OH sites inside of the support pore system. Furthermore, the Pt/Sn molar ratios of larger regions were studied by ESEM-EDX (area measured 500 nm×500 nm) to examine the presence of large aggregates and the homogeneity of the microcomposition of different regions. The following was observed: (a) the synthetic procedures produced small NPs well dispersed on the support; and, (b) using ESEM, distinct Pt/Sn ratios were measured depending on the analyzed region. In some regions, there was more Sn than Pt, which means that the decomposition of Sn precursors occurred also on the support sites.

Figure 6:
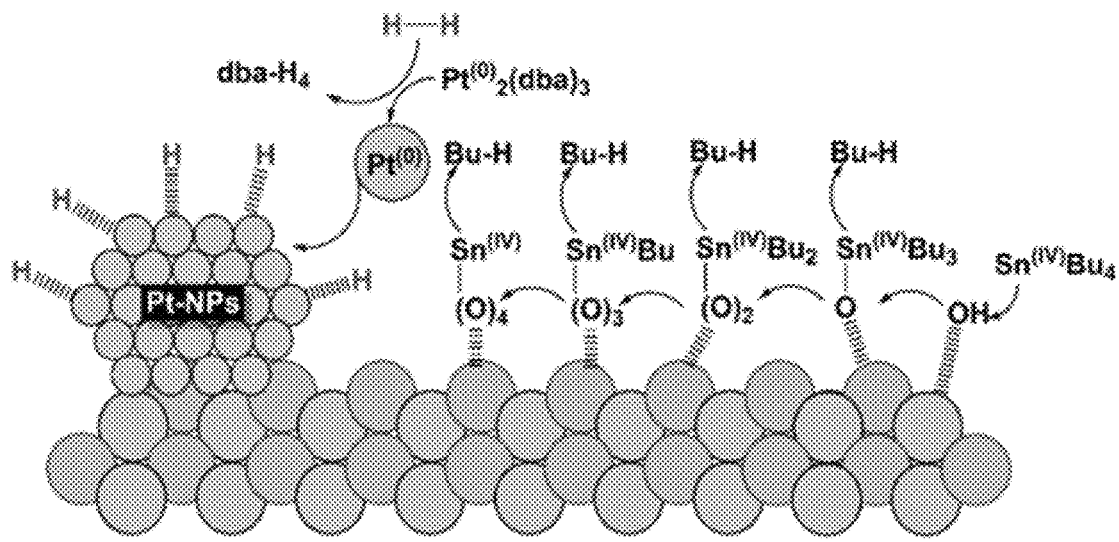
FIG. 6 schematically illustrates a proposed mechanism for the Sn and Pt precursors' decomposition onto supports.
Figure 6:
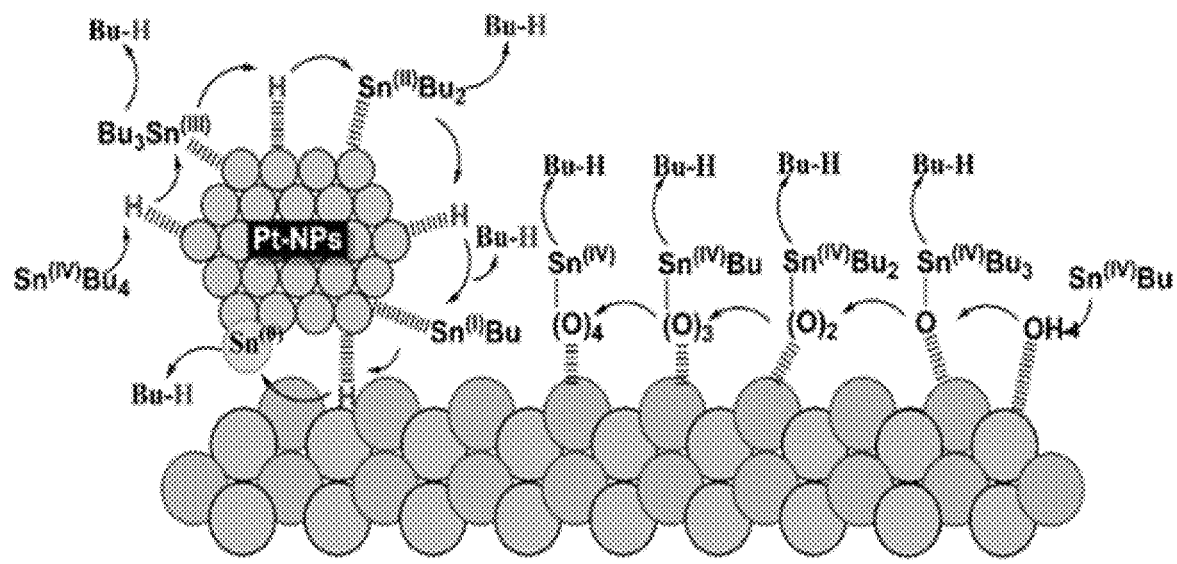

Without being bound to any theory, a possible mechanistic proposal of the Pt and Sn decomposition with the precursors is presented in the FIG. 6 (based on Basset. et al. (1998). Surface Organometallic Chemistry on Metals: Formation of a Stable: Sn(n-C$_4$H$_9$)n Fragment as a Precursor of Surface Alloy Obtained by Stepwise Hydrogenolysis of Sn (n-C$_4$H$_9$)$_4$ on a Platinum Particle Supported on Silica. *J. Am. Chem. Soc.* 120, 1, 137-146), The mechanism can be summarized in two steps: Step 1 (FIG. 6 (A)): Sn and Pt precursors start to react. Pt precursor (Pt$_2$(dba)$_3$) is hydrogenated, the hydrogenate dbaH$_4$ is released. Meanwhile, the Pt (0) naked metal atoms start to grow and nucleate starting to form the Pt—NP, having hydrides on its surface. At the same time the Sn precursor (Sn$^{(IV)}$ Bu$_4$, tetrabutyl tin) is reacting with the —OH groups present in the support, every time delivering a butane molecule; Step 2 (FIG. 6 (B)): once the Pt-NPs are formed, the Sn can react either with the support or with the Pt—NP.

Full characterization of selected PtSn nanocatalyts:

In this section, the characterization of the 4 bimetallic Pt/Sn systems stabilized with PPh$_3$ supported onto the four different supports (Al$_2$O$_3$ (Pt6c), Li—Al$_2$O$_3$ (Pt7c), Na-ZSM-5 (Pt8c), H-ZSM-5 (Pt9c)), is described. In Table 2 a characterization summary regarding the 4 bimetallic supported catalysts is presented.

HAADF-STEM. High-angle annular dark-field imaging scanning transmission electron microscopy images were obtained by the FEI TITAN. Mean diameters and particle distributions are displayed in Table 2. The average mean diameter is between 1.2-1.6 nm (Pt6c-Pt9c), confirming the small effect of the support on the nanoparticle's size.

SEM-EDX. Two different regions of the same sample (Pt6c) (one where NPs were analyzed and one where no NPs were present), spectrum 1 and spectrum 2, respectively, were analyzed by Scanning Electron Microscopy Energy Dispersive X-ray spectroscopy (SEM-EDX) (data not shown). In both cases a C signal was observed (coming from the support), Al and O (coming from the support) and the Pt and Sn contents vary depending on the zone of analysis. Even though no NPs were analyzed in spectrum 2, Sn was found in the EDX analysis, confirming the mechanism described previously. Therefore, it is important to control the Sn composition.

XRD. X-Ray Diffraction (XRD) patterns of the four Pt/Sn samples (Al$_2$O$_3$ (Pt6c), Li—Al$_2$O$_3$ (Pt7c), Na-ZSM-5 (Pt8c), H-ZSM-5 (Pt9c) were collected using a Bruker D8 Discover diffractometer and compared with the bare support. XRD patterns of the supported systems show only very small signal corresponding to the metal phase due to the low metal loading, the small size of the particle (i.e., smaller FWHM means larger particle size therefore smaller particle size results in broader peaks) and the support signal completely overlaid with the most intense signals arising from Sn and Pt (data not shown). Comparison of the diffraction pattern of the supported system on Al$_2$O$_3$ (Pt6c) (data not shown) with the colloidal bimetallic nanoparticle system Pt12 (Pt/Sn-PPh$_3$), previously commented, confirmed that the observed peaks correspond to the same crystalline phase (i.e., Pt phase peak with no shift due to the low Sn content on the final material).

TABLE 2

Characterization summary of bimetallic PtSn—PPh$_3$ supported nanocatalysts.

| Catalyst | Support | NPs size $^a$ (nm) | BET (m$^2$/g) | ICP Sn/Pt $^b$ (molar) | XPS Sn/Pt $^c$(molar) | XPS Sn(δ+)/ Sn(0) | XPS Pt(δ+)/ Pt(0) |
|---|---|---|---|---|---|---|---|
| Pt6c (Pt/Sn—PPh$_3$@Al$_2$O$_3$) | Al$_2$O$_3$ | 1.3 ± 0.3 | 126 | 1.04 | 1.51 | 20.7 | 0.4 |
| Pt7c (Pt/Sn—PPh$_3$@Li—Al$_2$O$_3$) | LiAl$_2$O$_3$ | 1.6 ± 0.3 | 122 | 0.66 | 1.24 | 4.3 | 0.2 |
| Pt8c (Pt/Sn—PPh$_3$@Na-ZSM5) | Na-ZSM5 | 1.3 ± 0.3 | 220 | 0.81 | 2.04 | 9.6 | 0.4 |
| Pt9c (Pt/Sn—PPh$_3$@H-ZSM5) | H-ZSM5 | 1.3 ± 0.3 | 391 | 0.78 | 1.19 | 12.0 | 0.4 |

$^a$ Particle size determined by measuring more than 200 nanoparticles randomly selected in the HAADF STEM images.
$^b$ Sn/Pt molar ratio determined from inductively coupled plasma optical emission spectrometry (ICP-OES) element analysis;
$^c$Sn/Pt, Sn(δ+)/Sn(0) and Pt(δ+)/Pt(0)molar ratio are determined from XPS analysis.

Surface area by Brunauer-Emmett-Teller (BET) analysis. The surface area results regarding the Pt/Sn samples (Al$_2$O$_3$ (Pt6c), Li—Al$_2$O$_3$ (Pt7c), Na-ZSM-5 (Pt8c), H-ZSM-5 (Pt9c)) were collected in Table 2. The difference of the area and pore volume values of the samples without and with NPs displayed are not significant and they were attributed to small different efficiency of the individual sample pretreatment (i.e., sample weighting process precision, real vacuum and temperature achieved in the pre-treatment, etc.). This means that there is a partial filling of the support pores without blocking them, and then, the catalytic performance of these materials can be compared. No significant difference in surface area and pore volume was observed when NPs are supported, indicating that there is a partial filling of the support pores without blocking them.

XPS. X-Ray Photoelectron Spectroscopy (XPS) analyses were conducted by using the SPECS PHOIBOS 150 spectrophotometer. The 4 bimetallic systems Pt/Sn samples (Al$_2$O$_3$ (Pt6c), Li—Al$_2$O$_3$ (Pt7c), Na-ZSM-5 (Pt8c), H-ZSM-5 (Pt9c)) were analyzed, and the obtained XPS spectra was treated with the CASAXPS software for estimation of the composition at the support surface as well as the estimated ratio between the different Pt and Sn species (See Table 2). The corresponding deconvolution was performed with the pertinent binding energies from Sn and Pt reported in the literature. Comparison of the bulk Sn/Pt ratios (ICP-OES values) and surface Pt/Sn ratios (XPS values) revealed the partial segregation of the Sn on the Pt surfaces (i.e., Pt-rich core and Sn-rich shell). The extend of this behavior depended on the support, the segregation order was: Na-ZSM-5 (Pt8c)>Al$_2$O$_3$ (Pt6c)>Li—Al$_2$O$_3$ (Pt7c)>H-ZSM-5 (Pt9c). Concerning the Sn(δ+)/Sn(0) ratio, the order was: Al$_2$O$_3$ (Pt6c)>H-ZSM-5 (Pt9c)>Na-ZSM-5 (Pt8c) >Li—Al$_2$O$_3$ (Pt7c). This difference was attributed to the different extend of the SnBu$_4$ reaction with the support surfaces species resulting in more Sn$_{IV}$ species (i.e., Sn$^{IV}$Bu$_4$+4 Al—OH═Sn$^{IV}$(AlO)$_4$+Bu-H) than for the catalyst in which SnBu$_4$ preferably reacts with Pt—NP hydrides (n Pt$^0$-NPs-H+Sn$^{IV}$Bu$_4$═Pt$^0_n$,Sn$^0$-NPs+4 Bu—H). Concerning the Pt(δ+)/Pt(0) ratio, the order was somehow very similar to Sn(δ+)/Sn(0) ratio order:(Al$_2$O$_3$ (Pt6c)═H-ZSM-5 (Pt9c)═Na-ZSM-5 (Pt8c)>Li—Al$_2$O$_3$ (Pt7c). This behavior was ascribed to the protecting effect against oxidation provided by the Sn-species on the Pt (0) surface atoms.

Examples 1 and 2 show that several combinations of porous supports, organic stabilizing agents, and organometallic precursors can be used to achieve the catalytic compositions of the invention in a simple process of preparation. The process is free of any pretreatment of the supports with any cocatalyst and/or any calcination step after addition of the catalyst, and any further deposition of the catalyst promoters. Moreover, the process does not involve any sequence of tedious steps implying different temperatures.

Example 3. Preparation of Nanocatalysts of PtSn with Sn(II) Precursors 3.1. Assay of the Organic Stabilizing Agent in PtSn Colloidal NPs with Sn(II) Precursors The preparation of colloidal PtSn nanoparticles was carried out by decomposition of the Pt$_2$ (dba)$_3$ and N,N'-Di-t-butyl-2,3-diamidobutane tin (abbreviated Sn(II) C12H26N2) precursors. The decomposition was carried out under 3×10$^5$ Pa H$_2$ atmosphere either at room temperature or at 100° C. using Pt$_2$(dba)$_3$ and N,N'-Di-t-butyl-2,3-diamidobutane tin (abbreviated Sn(II) C12H26N2) precursors as organometallic precursors, and PPh$_3$ and N-heterocyclic carbene as organic stabilizing agent. Different solvents (tetrahydrofuran and toluene) and temperatures (room temperature and 100° C.) were also assayed. The decomposition of the Pt and Sn precursors at 100° C. was monitored by measuring the Pt and Sn content by inductively coupled plasma Optical Emission Spectroscopy (ICP-OES) and SEM-EDX, the nanoparticle mean diameter and dispersion measured by HAADF-STEM and the crystalline phase was studied by XRD (see Table 3).

TABLE 3

Characterization summary of bimetallic PtSn colloidal NPs with Sn(II) precursors.

| Catalyst | NPs size$^a$ (nm) | ICP Sn/Pt$^b$ (molar) | XRD phases/ crystallite size (nm)) |
|---|---|---|---|
| Pt 17 (PtSn-r.t) | 2.7 ± 1.6 | 1.53 | Pt fcc/1.61 nm |
| Pt18 (PtSn-100) | 4.9 ± 1.9 | 1.23 | PtSn hexagonal/4.80 nm |
| Pt19 (PtSn-NHC-r.t.) | 2.5 ± 0.9 | 1.28 | Pt fcc/0.93 nm |
| Pt20 (PtSn-NHC-100) | 5.0 ± 3.0 | 1.25 | PtSn hexagonal/3.14 nm |
| Pt21 (PtSn-PPh$_3$-r.t.) | 1.9 ± 0.8 | 1.49 | Pt fcc/0.53 nm |
| Pt22 (PtSn-PPh$_3$-100) | 2.3 ± 1.0 | 1.28 | Pt fcc/0.77 nm (after termal at 900° C. treatment PtSn hexagonal and Pt$_2$Sn$_3$ hexagonal) |

$^a$ Particle size determined by measuring more than 200 nanoparticles randomly selected in the HAADF STEM images.
$^b$ Sn/Pt molar ratio determined from inductively coupled plasma optical emission spectrometry (ICP-OES) elemental analysis;
$^c$ Crystalline phase and crystalline size determined by XRD.

Bimetallic PtSn-r.t. (Pt17) were prepared using Pt$_2$(dba)$_3$ and N,N'-Di-t-butyl-2,3-diamidobutane tin as organometallic precursors in a Pt/Sn molar ratio 1:1, in the absence of stabilising agent and using tetrahydrofuran at r.t under 3 bar of H$_2$. Pt17 displayed a size of 2.7±1.6 nm by TEM. The XRD diffractogram of Pt17 showed a Pt fcc predominant crystallite phase and a crystallite size of 1.61 nm, meaning the NPs measured are approximately 1.5 times the crystallite size.

By comparison the same colloidal PtSn-100 Pt18 without any stabilising agent were prepared but this time, heating the reaction mixture at 100° C. Pt18 displayed agglomerates showing a size of 4.9±1.9 nm by TEM. The XRD diffractogram of Pt18 showed a PtSn hexagonal predominant crystallite phase and a crystallite size of 4.80 nm, matching with the TEM obtained size.

The effect of the ligands was studied as well (under 3 bars of H$_2$) by using N-heterocyclic carbene (NHC—CO$_2$) or triphenylphosphine (PPh$_3$) with tetrahydrofuran or toluene. In the presence of NHC, if r.t. is used, small and well-dispersed nanoparticles of 2.5±0.9 nm are obtained (PtSn—NHC-r.t. NPs (Pt19)). The XRD diffractogram of Pt19 showed a Pt fcc predominant crystallite phase and a crystallite size of 0.93 nm, meaning the NPs measured are approximately 2 times the crystallite size. The large differences observed by TEM and XRD could suggest that particles observed by TEM were formed by several separated crystals or that the resolution of transmission microscope did not allow the detection of nanoparticles smaller than 1 nm.

If the reaction takes place at 100° C., small agglomerates of 5.0±3.0 nm are obtained (PtSn—NHC-100 (Pt20)). In this case, the effect of the temperature promotes the agglomeration of the NPs. The XRD diffractogram of Pt20 showed a PtSn hexagonal predominant crystallite phase and a crystallite size of 3.14 nm. In this case the size of the nanoparticle does not coincide with the measured in TEM. The minimum unit (crystallite) is estimated around 3.0 nm.

In the presence of PPh$_3$, if r.t. is used, small and well-dispersed nanoparticles of 1.87±0.83 nm are obtained (PtSn-PPh$_3$-r.t. NPs (Pt21)). The XRD diffractogram of Pt21 showed a Pt fcc predominant crystallite phase and a crystallite size of 0.57 nm, meaning the NPs measured are approximately 2 times the crystallite size.

If the reaction takes place at 100° C., also small and well-dispersed nanoparticles of 2.33±1.05 nm are obtained (PtSn-PPh$_3$-100 (Pt22)). Concerning the XRD of Pt22, it showed a Pt fcc predominant crystallite size of 0.57 nm. It is worth mentioning that here if the temperature increases (from r.t. to 100° C.), it does not show a direct effect on the crystalline phase, because the Pt fcc phase is maintained, and no alloy is formed. In the original diffractogram the predominant Pt band at 39.76° is particularly displaced and a possible shoulder could have appeared around 36°. For that reason, to confirm that the sample does not uniquely contains Pt NPs, a calcination at 900° C. was performed of Pt22 and the XRD diffraction pattern was studied again. After the heat treatment, the broadness of the bands characteristic of NPs disappeared and the nanoparticles grew. Furthermore, two different alloy phases arise: PtSn hexagonal and Pt$_2$Sn$_3$ hexagonal. The binary phase diagram of the PtSn system was examined, and according to it, the PtSn and Pt$_2$Sn$_3$ phases cannot have been formed by temperature. For this reason, only the crystallinity of PtSn and Pt$_2$Sn$_3$ NPs must have increased, and the alloys are more accurately detectable. As a result, this experiment makes clear that the synthesis of colloidal NPs with PPh$_3$ ligand at 100° C. leads to bimetallic NPs.

PPh$_3$ moiety appears to be a suitable ligand for the preparation of small-sized and well-distributed nanoparticles formed by the decomposition of Pt2(dba)$_3$ and N,N'-Di-t-butyl-2,3-diamidobutane tin, independently of the temperature used. These results thus provided evidence of the importance of the organic stabilizing agent for the one-step preparation of PtSn NPs by the organometallic approach. $^{31}$P NMR analyses of the washing solutions showed no phosphorous-signal suggesting that the phosphorus-compounds remained in the catalyst surfaces.

The molar relation of Pt: Sn was assessed by ICP-OES and it was lower than the initially added, although closer to the nominal value of 1 when the nanoparticles were prepared at 100° C. Comparison of the bimetallic PtSn NPs (Pt17, Pt18) without ligand, and with N-heterocyclic carbene (Pt19, Pt20) or PPh$_3$(Pt21, P22), revealed the importance of the organic stabilizing agent for the one-step preparation of PtSn-NPs by the organometallic approach.

The results showed that both Pt$^{(0)}_2$ (dba)$_3$ and the N,N'-Di-t-butyl-2,3-diamidobutane tin (abbreviated Sn(II) C12H26N2) quantitatively decomposes over a relatively short period of time (<15-20 h.). In contrast, in example 2, Sn(IV) and Sn(II) only partially decomposed.

Thus, this methodology allows the preparation of PtSn-nanocatalyst with different Sn loading depending on the precursor. All tested conditions were, thus, working conditions for the preparation of the catalysts.

3.2. Supported Bimetallic Pt—Sn—NPs with Sn(II) Precursors

The decomposition of the Pt$_2$(dba)$_3$ and N,N'-Di-t-butyl-2,3-diamidobutane tin (abbreviated Sn(II) C12H26N2) precursors onto the two supports Al$_2$O$_3$ and H-ZSM5 was carried out. The decomposition was carried out under 3×10$^5$ Pa H$_2$ atmosphere either at room temperature or at 100° C. using Pt$_2$ (dba)$_3$ and N,N'-Di-t-butyl-2,3-diamidobutane tin (abbreviated Sn(II) C12H26N2) precursors as organometallic precursors, and PPh$_3$ and N-heterocyclic carbene as organic stabilizing agent. These samples presented a nominal metal loading of Pt 2% wt-Sn 1% wt. (Pt/Sn molar ratio is 1:1) and they were labeled Pt23 (Al$_2$O$_3$ and N-heterocyclic carbene at 100° C.), Pt24 (Al$_2$O$_3$ and PPh$_3$ at room temperature), Pt25 (Al$_2$O$_3$ and PPh$_3$ at 100° C.), and Pt26 (H-ZSM-5 and PPh$_3$ at 100° C.). The decomposition of the Pt and Sn precursors at 100° C. was monitored by measuring the Pt and Sn content by inductively coupled plasma Optical Emission Spectroscopy (ICP-OES) and SEM-EDX, the nanoparticle mean diameter and dispersion measured by HAADF-STEM and the crystalline phase was studied by XRD (see Table 4).

PtSn nanoparticles prepared using PPh$_3$ as stabilizing agent displayed small mean diameters. The mean diameter is smaller for the sample prepared at 100° C. Pt25 (1.4±0.3) than those prepared at room temperature Pt24 (1.8±0.3 nm). Regarding the NHC ligand, Pt26 presented similar nanoparticle mean diameter (1.5±0.3 nm) than Pt24 and Pt25. Pt26 displayed small nanoparticle mean diameters (1.5±0.3 nm) but slightly larger than those obtained with the same conditions with Al$_2$O$_3$ support.

TABLE 4

Characterization summary of supported bimetallic Pt—Sn-NPs with Sn(II) precursors.

| Catalyst | NPs size [a] (nm) | ICP Sn/Pt [b] (molar) |
|---|---|---|
| Pt23 (Pt(2%)/Sn(1%)-NHC@Al$_2$O$_3$ (100° C.)) | 2.0 ± 0.9 | 1.14 |
| Pt24 (Pt(2%)/Sn(1%)-PPh$_3$@Al$_2$O$_3$ (r.t.)) | 1.8 ± 0.3 | 1.14 |
| Pt25 (Pt(2%)/Sn(1%)-PPh$_3$@Al$_2$O$_3$ (100° C.)) | 1.4 ± 0.3 | 1.18 |
| Pt26 (Pt(2%)/Sn(1%)-PPh$_3$@H-ZSM5 (Si/Al 50) (100° C.)) | 1.6 ± 0.3 | 1.33 |

[a] Particle size determined by measuring more than 200 nanoparticles randomly selected in the HAADF STEM images.
[b] Sn/Pt molar ratio determined from inductively coupled plasma optical emission spectrometry (ICP-OES) elemental analysis.

A comparison of the colloidal nanoparticles described previously in the table above (Table 3) with the supported ones described herein (Table 4), regarding the nanoparticle size was made. Smaller nanoparticle mean diameter and narrower dispersions were measured for supported systems (1.4-2.0, see table 4) than those measured for the colloidal system (i.e., 1.9-5.0, see table 3).

Regarding the ICP-OES, slightly lower Sn/Pt (mol/mol) ratios were measured for supported systems (1.13-1.18, see table 4) than those measured for the colloidal system (i.e., 1.23-1.53, see table 3).

Regarding the XRD, for all the supported catalyst in this section (Pt23 to Pt25) no peaks related to the metals were detected and the diffractograms obtained were directly the same as the bare support. This is due to the amount of metal present on the catalyst is in the range of 1.0-2.0%.

PPh$_3$ moiety appears to be a suitable stabilizing agent for the preparation of small-sized and well-distributed supported nanoparticles formed by the decomposition of Pt$_2$ (dba)$_3$ and N,N'-Di-t-butyl-2,3-diamidobutane tin, independently of the temperature and support used. These results thus, again, provided evidence of the importance of the organic stabilizing agent for the one-step preparation of PtSn NPs by the organometallic approach. $^{31}$P NMR analyses of the washing solutions showed no phosphorous-signal suggesting that the phosphorus-compounds remained in the catalyst surfaces.

The results obtained revealed that (data not shown): (a) Pt-precursor was quantitatively decomposed forming small Pt-NPs and the decomposition rate was not affected by the nature of the support; (b) Sn-precursor was quantitatively decomposed. Furthermore, the Pt/Sn molar ratios of larger regions were studied by ESEM-EDX (area measured 500 nm×500 nm) to examine the presence of large aggregates and the homogeneity of the microcomposition of different regions. The following was observed: (a) the synthetic procedures produced small NPs well dispersed on the support; and, (b) using ESEM, distinct Pt/Sn ratios were measured depending on the analyzed region. In some regions, there was more Sn than Pt, which means that the decomposition of Sn precursors occurred also on the support sites.

Without being bound to any theory, a possible mechanistic proposal of the Pt and Sn decomposition with the precursors is presented in the FIG. 6 (based on Basset. et al. (1998)).

Example 4. Preparation of Nanocatalysts of PtGa with Ga Precursors 4.1. Assay of the Organic Stabilizing Agent in PtGa Colloidal NPs The preparation of colloidal PtGa nanoparticles was carried out by decomposition of the Pt$_2$(dba)$_3$ and trimethyl gallium (GaMe$_3$) precursors. The decomposition was carried out under 3×10$^5$ Pa H$_2$ atmosphere either at room temperature or at 100° C. using Pt$_2$(dba)$_3$ and trimethyl gallium (GaMe$_3$) precursors as organometallic precursors, and PPh$_3$ and N-heterocyclic carbene as organic stabilizing agent. Different solvents (tetrahydrofuran and toluene) and temperatures (room temperature and 100° C.) were also assayed. The decomposition of the Pt and Ga precursors at 100° C. was monitored by measuring the Pt and Sn content by inductively coupled plasma Optical Emission Spectroscopy (ICP-OES) and SEM-EDX, the nanoparticle mean diameter and dispersion measured by HAADF-STEM and the crystalline phase was studied by XRD (see Table 5).

Bimetallic PtGa-NPs were prepared using Pt$_2$(dba)$_3$ and trimethyl gallium in a Pt/Ga molar ratio 1:1, with carbene (Pt27) and triphenylphosphine ligand (Pt28) using tetrahydrofurane and toluene, respectively, at 100° C. for 20 h under 3 bar of H$_2$.

Concerning the nanoparticle size, PtGa—NHC (Pt27) displayed smaller nanoparticle mean diameter and narrower distributions than PtGa-PPh3 (Pt28). Concerning the Pt/Ga molar ratios, PtGa—NHC (Pt27) displayed slightly smaller Pt/Ga molar ratios than PtGa-PPh3 (Pt28).

TABLE 5

Characterization summary of bimetallic PtGa colloidal NPs.

| Catalyst | NPs size $^a$ (nm) | ICP Ga/Pt $^b$ (molar) |
|---|---|---|
| Pt27 (PtGa-NHC-100) | 0.8 ± 0.2 | 1.20 |
| Pt28 (PtGa-PPh$_3$- 100) | 1.4 ± 0.4 | 1.13 |

$^a$ Particle size determined by measuring more than 200 nanoparticles randomly selected in the HAADF STEM images.
$^b$ Sn/Pt molar ratio determined from inductively coupled plasma optical emission spectrometry (ICP-OES) elemental analysis.

Both bimetallic PtGa NPs with N-heterocyclic carbene (Pt27) and PPh$_3$ (Pt28), revealed the importance of the organic stabilizing agent for avoiding the formation of aggregates and stabilizing small and well-dispersed nanoparticles. These results thus provided evidence of the importance of the organic stabilizing agent for the one-step preparation of PtSn-NPs by the organometallic approach. As a mode of characterization of the nanoparticles, $^{31}$P NMR analyses of the washing solutions of PtGa NPs with PPh$_3$ (Pt28) showed that phosphorus-compounds remained in the catalyst surfaces.

The results showed that Pt$^{(0)}$$_2$ (dba)$_3$ and GaMe$_3$ quantitatively decomposes over a period of time of <15-20 h, and the precursors work well within the desired yield of synthesis of the catalysts. All tested conditions were, thus, working conditions for the preparation of the catalysts.

4.2. Supported bimetallic Pt—Ga—NPs

The decomposition of the Pt$_2$(dba)$_3$ and trimethyl gallium (GaMe$_3$) precursors onto the four supports, Al$_2$O$_3$, Li—Al$_2$O$_3$, Na-ZSM5 and H-ZSM5, was carried out. The decomposition was carried out at 100° C. using Pt$_2$(dba)$_3$ and trimethyl gallium (GaMe$_3$) precursors as organometallic precursors, and PPh$_3$ and N-heterocyclic carbene as organic stabilizing agent. These samples presented a nominal metal loading of Pt 2% wt-Ga 1% wt. (Pt/Ga molar ratio is 1:1) and they were labelled Pt29 (Al$_2$O$_3$ and PPh$_3$), Pt30 (Li—Al$_2$O$_3$ and PPh$_3$), Pt31 (H-ZSM-5 and PPh$_3$) and Pt32 (Na-ZSM-5 and PPh$_3$). The decomposition of the Pt and Ga precursors at 100° C. was monitored by measuring the Pt and Sn content by inductively coupled plasma Optical Emission Spectroscopy (ICP-OES) and SEM-EDX, the nanoparticle mean diameter and dispersion measured by HAADF-STEM and the crystalline phase was studied by XRD (see Table 6).

TABLE 6

Characterization summary of bimetallic PtGa supported NPs.

| Catalyst | NPs size $^a$ (nm) | ICP Ga/Pt $^b$ (molar) |
|---|---|---|
| Pt29 (Pt(2%)/Ga(1%)-PPh$_3$@ Al$_2$O$_3$ (100° C.)) | 1.4 ± 0.4 | 1.13 |
| Pt30 (Pt(2%)/Ga(1%)-PPh$_3$@Li(0.45%)Al$_2$O$_3$ (100° C.)) | 1.2 ± 0.3 | 1.51 |
| Pt31 (Pt(2%)/Ga(1%)-PPh$_3$@NaZSM5 (Si/Al 40) (100° C.)) | 1.4 ± 0.3 | 1.63 |
| Pt32 (Pt(2%)/Ga(1%)-PPh$_3$@HZSM5 (Si/Al 40) (100° C.)) | 1.3 ± 0.3 | 1.68 |

$^a$ Particle size determined by measuring more than 200 nanoparticles randomly selected in the HAADF STEM images.
$^b$ Sn/Pt molar ratio determined from inductively coupled plasma optical emission spectrometry (ICP-OES) elemental analysis.

A comparison of the colloidal nanoparticles described previously in the table above (Table 5) with the supported ones described herein (Table 6), regarding the nanoparticle size was made. Similar nanoparticle mean diameter and narrower dispersions were measured for supported systems (1.2-1.4, see table 5) than those measured for the colloidal system (i.e., 1.4, see table 6).

Regarding the ICP-OES, the Ga/Pt molar ratios measured for supported systems depend on the support, but in general, the values (1.13-1.68, see table 6) are lower than those measured for the colloidal system (i.e., 1.13-1.20, see table 5).

Regarding the XRD, for all the supported catalysts in this section (Pt29 to Pt32) no peaks related to the metals were detected and the diffractograms obtained were directly the same as the bare support. This is due to the amount of metal present on the catalyst is in the range of 1.0-2.0%.

PPh$_3$ moiety appears to be a suitable stabilizing agent for the preparation of small-sized and well-distributed supported nanoparticles formed by the decomposition of Pt$_2$ (dba)$_3$ and trimethyl gallium (GaMe$_3$), independently of the temperature and support used. These results thus provided evidence of the importance of the organic stabilizing agent for the one-step preparation of PtSn NPs by the organometallic approach. $^{31}$P NMR analyses of the washing solutions showed no phosphorous-signal suggesting that the phosphorus-compounds remained in the catalyst surfaces.

The results obtained revealed that (data not shown): (a) Pt-precursor was quantitatively decomposed forming small Pt-NPs and the decomposition rate was not affected by the nature of the support; (b) Ga-precursor was partially decomposed (i.e., 70 to 90%) and the decomposition rate varied depending on the support in the order Al$_2$O$_3$>Li—Al$_2$O$_3$ no support (behavior attributed to the presence of proton with amphoteric character in the alumina surface, i.e., Al—OH groups); and (c) GaMe$_3$ in the presence of PPh$_3$ and Al$_2$O$_3$ decomposed quite fast (70% and 90% after 20 and 40 h, respectively).

Furthermore, the Pt/Ga molar ratios of larger regions were studied by ESEM-EDX (area measured 500 nm×500 nm) to examine the presence of large aggregates and the homogeneity of the microcomposition of different regions. The following was observed: (a) the synthetic procedures produced small NPs well dispersed on the support; and, (b) using ESEM, distinct Pt/Ga ratios were measured depending on the analyzed region. In some regions, there was more Ga than Pt which, means that the decomposition of Ga precursors occurred also on the support sites.

Without being bound to any theory, a possible mechanistic proposal of the Pt and Ga system, and since Sn (group 14) and Ga (group 13) organometallic precursors display similar reactivity, could be related to the above decomposition mechanism of the Pt and Sn presented in the FIG. 6 (based on Basset. et al. (1998)).

Example 5. Preparation of Nanocatalysts of NiSn with Sn Precursors 5.1. Assay of the Organic Stabilizing Agent in NiSn Colloidal NPs with Sn Precursors The preparation of colloidal NiSn nanoparticles was carried out by decomposition of the $Ni(COD)_2$ and $SnBu_4$ precursors. The decomposition was carried out under $3\times10^5$ Pa $H_2$ atmosphere either at room temperature or at 100° C. using $Ni(COD)_2$ and $SnBu_4$ precursors as organometallic precursors, and $PPh_3$ and N-heterocyclic carbene as organic stabilizing agent. Different solvents (tetrahydrofuran and toluene) and temperatures (room temperature and 100° C.) were also assayed. The decomposition of the Ni and Sn precursors was monitored by measuring the Pt and Sn content by inductively coupled plasma Optical Emission Spectroscopy (ICP-OES), Gas Chromatography (GC-TCD) analysis of the products in the gas phase generated by decomposition of the precursors and SEM-EDX, the nanoparticle mean diameter and dispersion measured by HAADF-STEM and the crystalline phase was studied by XRD.

Bimetallic NiSn-NPs (Ni1) were prepared using $Ni(COD)_2$ and $SnBu_4$ as organometallic precursors in a Ni/Sn molar ratio 1:1, with N-heterocyclic carbene and using tetrahydrofuran at 100° C. under 3 bar of H2. Ni1 displayed ultra-small NPs size less than 1.5 nm by TEM.

Bimetallic NiSn-NPs (Ni2) were prepared using $Ni(COD)_2$ and $SnBu_4$ as organometallic precursors in a Ni/Sn molar ratio 1:1, with $PPh_3$ and using toluene at 100° C. under 3 bar of H2. Ni2 displayed ultra-small NPs size less than 1.5 nm by TEM.

Then, different solvents (tetrahydrofuran and toluene) and temperatures (room temperature and 100° C.) were also assayed. The decomposition of the Ni and Sn precursors at 100° C. was monitored by measuring the Ni and Sn content by inductively coupled plasma Optical Emission Spectroscopy (ICP-OES) and Scanning electron microscopy (SEM): EDS (Energy Dispersive X-rays spectroscopy), and the crystalline phase was studied by XRD.

The results showed that the $Ni(COD)_2$ precursor decomposes quantitatively over a period of time of <15-20 h, and the $SnBu_4$ partially decomposes (2-10%) over a period of time of >40 h.

5.2. Supported Bimetallic Ni—Sn—NPs with Sn Precursors

The decomposition of the $Ni(COD)_2$ and $SnBu_4$ precursors onto the two supports $Al_2O_3$ and $Li(0.46\%)$-$Al_2O_3$ was carried out. The decomposition was carried out at 100° C. using $Ni(COD)_2$ and $SnBu_4$ precursors as organometallic precursors, and $PPh_3$ and N-heterocyclic carbene as organic stabilizing agent. These samples presented a nominal metal loading of Ni 2% wt-Sn 3.75% wt. (Ni/Sn molar ratio is 1:1) and they were labeled Ni3 ($Al_2O_3$ and $PPh_3$), Ni4 ($Al_2O_3$ and NHC), Ni5 (Li—$Al_2O_3$ and $PPh_3$) and Ni6 (Li—$Al_2O_3$ and NHC). The decomposition of the Ni and Sn precursors at 100° C. was monitored by measuring the Ni and Sn content by inductively coupled plasma Optical Emission Spectroscopy (ICP-OES) and SEM-EDX, the nanoparticle mean diameter and dispersion measured by HAADF-STEM and the crystalline phase was studied by XRD.

TABLE 7

Characterization summary of bimetallic NiSn supported NPs.

| Catalyst | NPs size [a] (nm) | ICP Sn/Ni [b] (molar) |
|---|---|---|
| Ni3 (Ni(2%)/Sn(3.75%)-$PPh_3$@ $Al_2O_3$ (100° C.)) | 3.8 ± 0.9 | 0.34 |
| Ni4 (Ni(2%)/Sn(3.75%)-NHC@ $Al_2O_3$ (100° C.)) | 9.7 ± 1.7 | 0.06 |
| Ni5 (Ni(2%)/Sn(3.75%)-$PPh_3$@ Li—$Al_2O_3$ (100° C.)) | 2.3 ± 0.7 | 0.39 |

[a] Particle size determined by measuring more than 200 nanoparticles randomly selected in the HAADF STEM images.
[b] Sn/Pt molar ratio determined from inductively coupled plasma optical emission spectrometry (ICP-OES) elemental analysis.

Regarding the ICP-OES, the Sn/Ni molar ratios measured for supported systems depend on the stabilizing agent, in general, the values with PPh3 (0.34-0.39, see table 7 are higher than with NHC (i.e., 0.06, see table 7).

Regarding the XRD, for all the supported catalysts in this section (Ni3 to Ni4) no peaks related to the metals were detected and the diffractograms obtained were directly the same as the bare support. This is due to the amount of metal present on the catalyst is in the range of 1.0-2.0%.

$PPh_3$ moiety appears to be a suitable stabilizing agent for the preparation of small-sized and well-distributed supported nanoparticles formed by the decomposition of $Ni(COD)_2$ and $SnBu_4$, independently of the temperature and support used. These results thus provided evidence of the importance of the organic stabilizing agent for the one-step preparation of NiSn NPs by the organometallic approach. $^{31}P$ NMR analyses of the washing solutions showed no phosphorous-signal suggesting that phosphorus-compounds remained in the catalyst surfaces.

The results obtained revealed that (data not shown): (a) Ni-precursor was quantitatively decomposed forming small Ni-NPs and the decomposition rate was not affected by the nature of the support; (b) Sn-precursor was partially decomposed and the decomposition rate varied depending on nature of stabilizing agent in the order $PPh_3$>>N-heterocyclic carbene, and the support in the order $Al_2O_3$>Li—$Al_2O_3$ no support (behavior attributed to the presence of proton with amphoteric character in the alumina surface, i.e., Al—OH groups); and (c) $SnBu_4$ in the presence of $PPh_3$ and $Al_2O_3$ decomposed 35-45% after 40 h; and $SnBu_4$ in the presence of N-heterocyclic carbenes and $Al_2O_3$ decomposed 7-10% after 40 h.

Furthermore, the Ni/Sn molar ratios of larger regions were studied by ESEM-EDX (area measured 500 nm×500 nm) to examine the presence of large aggregates and the homogeneity of the microcomposition of different regions. The following was observed: (a) the synthetic procedures produced small NPs well dispersed on the support; and, (b) using ESEM, distinct Ni/Sn ratios were measured depending on the analyzed region. In some regions, there was more Sn than Ni, which means that the decomposition of Sn precursors occurred also on the support sites.

Without being bound to any theory, a possible mechanistic proposal of the Ni and Sn system, and since Pt and Ni belong to group 10, could be related to the above decomposition mechanism of the Pt and Sn presented in the FIG. 6 (based on Basset. et al. (1998)).

Example 6. N-ODH with Bimetallic Nanocatalyst

The samples of Example 2 (Pt/Sn-nanocatalyst with $Al_2O_3$ and $PPh_3$ (Pt6c), Li—$Al_2O_3$ and $PPh_3$ (Pt7c), Na-ZSM-5 and $PPh_3$ (Pt8c), H-ZSM-5 and $PPh_3$ (Pt9c)), Example 3 (Pt/Sn-nanocatalyst with Al$_2$O$_3$ and N-heterocyclic carbene (Pt23), Al$_2$O$_3$ and PPh$_3$ (Pt25) and H-ZSM-5 and PPh$_3$ (Pt26)), Example 4 (Pt/Ga nanocatalyst with Al$_2$O$_3$ and PPh$_3$ (Pt29), Li—Al$_2$O$_3$ and PPh$_3$ (Pt30), H-ZSM-5 and PPh$_3$ (Pt31) and Na-ZSM-5 and PPh$_3$ (Pt32) and Example 5 (Ni/Sn nanocatalyst with Al$_2$O$_3$ and PPh$_3$ (Ni3), Al$_2$O$_3$ and N-heterocyclic carbene (Ni4), Li—Al$_2$O$_3$ and PPh$_3$ (Ni5) and Li—Al$_2$O$_3$ and N-heterocyclic carbene (Ni6)) were then evaluated in the non-oxidative dehydrogenations (n-ODH) (i.e., n-ODH of propane for the selective production of propylene and n-ODH of butane/butylene for the selective production of butadiene) and aromatization reactions (propane aromatization for the production of benzenes). All were working catalysts for the desired reaction.

The catalytic set up for the non-oxidative dehydrogenation reactions consisted in a stainless-steel fixed bed reactor system on-line connected to a GC-TCD/MS system. The reaction was carried out under O$_2$ and H$_2$O exclusion conditions. Argon (5.0, purity 99.999%), N$_2$ (5.0, purity 99.999%), H$_2$ (5.0, purity 99.999%), propane (3.5, purity 99.95%), butane (3.5, purity 99.95%) and 2-butene (3.5, purity 99.95%) were purified in line with molecular sieves and BTS-catalysts traps to ensure high purity was maintained. Mass flow controllers and by-pass 3 port valve system controlled the composition and the flow to the reactor or directly to the analysis system. Pressure was monitored and controlled: (a) pressure transducer at the entrance of the reactor, (b) a pressure regulator with a manometer at the exit of the reactor, and (c) safety valves for avoiding overpressures (adjusted to a maximum of 5 bars). Temperature was controlled with a temperature heating jacket Hobersal with a thermocouple inside the reactor.

Initially, experiments were completed for the set-up of the reaction system including calibration of the mass flow controllers and preparation of temperature programs for heating the reaction without over-heating the catalyst. Later, the analytical methods were prepared by injecting standard gas samples in the GC-TCD/MS systems, thus, allowing the identification of reaction products, the preparation of calibration curves and the determination of the response factors. For catalytic tests, the catalyst preparation was carried out in the glovebox for avoiding oxidation. The catalyst 1-100 mg (i.e., 25.0 mg cat., 0.1 mg Pt) was dispersed in a known amount of silicon carbide (∅≈150-300 μm) and placed in the reactor. Catalyst pre-treatment consists in a reduction program at 500-600° C. (1° C./min) under H$_2$ flow for 4-16h at a pressure comprised between 0.5 and 3 absolute bars.

For example, the selected initial conditions for the non-oxidative dehydrogenation (n-ODH) of propane were: temperature, 530° C.; pressure, 1 bar; and gas flow: 3 mL/min of Propane, 21 mL/min of Ar and 1 mL/min H$_2$.

The propane conversion and propene selectivity were determined by gas chromatographic (GC-TCD) analysis of gas samples taken at regular intervals (each 14 min). The response factors of the propane and propene were determined using argon as internal standard. The mathematical formula for the determination of the conversion and selectivity are:

$$\text{Propane conversion (\%)} = \frac{\text{Total Propane}_{out}}{\text{Total Propane}_{in}} \times 100$$

$$\text{Propylene selectivity (\%)} = \frac{\text{Total propylene}_{out}}{\text{Total propane}_{in} - \text{Total propane}_{out}} \times 100$$

Next Table 8(a) lists the results obtained on propane dehydrogenation (PDH) by non-oxidative dehydrogenation with some of the catalysts compositions of the invention. Comparative data with the benchmark Statoil catalyst (currently termed LINDE-Basf Statoil) are also included.

TABLE 8a

Propane dehydrogenation (PDH) catalyzed by Pt/Sn and Ni/Sn nanocatalyst.

| Name | Composition | Initial conv. -to - conv. After 900 min (%) | Selectivity (%) |
|---|---|---|---|
| STATOIL Reference | PtSn/Mg(Al)O; | 26-to-3 | 83 |
| Pt6c | PtSn-PPh$_3$/Al$_2$O$_3$ | 24-to-15 | 98 |
| Pt7c | PtSn-PPh$_3$/Li—Al$_2$O$_3$; | 20-to-10 | 97 |
| Pt 25 | PtSn-PPh3/Al2O3 | 23-to-12 | 99 |
| Pt 29 | PtGa-PPh3/Al2O3 | 23-to-14 | 99 |
| Ni3 | NiSn-PPh$_3$/Al$_2$O$_3$ | 2-to-1.5 | 75 |

The Statoil Catalyst (SnPt/Mg(Al)O) (US2005003960A1, STATOIL ASA, incorporated herein by reference) is agreed as the benchmark catalyst for the set-up of the reaction and analytical methodology. For comparative purpose, in present example it was tested in PDH in the same reaction conditions than our catalyst. Catalytic tests with bimetallic Pt/Sn catalyst (Al$_2$O$_3$ (Pt6c and Pt25), Li—Al$_2$O$_3$ (Pt7c)), Pt/Ga catalyst (Pt29) and the Ni/Sn catalyst (Al$_2$O$_3$ and PPh$_3$ (Ni3)) provided more competitive performances respect to the benchmark catalyst. These catalysts provide highly selective (selectivity higher than 99%) transformation of propane feeds with much higher conversion rates (23-25% at 530° C. and 1 bar) and stabilities than the reference catalysts. The Pt/Sn catalyst Pt—Sn—PPh$_3$/Al$_2$O$_3$ (Pt6c) provided the highest initial conversion (23.6%) and it was progressively deactivated until reaching 11.5% after 3000 min of TOS. In terms of product selectivity, the alumina-based catalysts Pt—Sn-PPh$_3$/Al$_2$O$_3$ (Pt6c) and Pt—Sn-PPh$_3$/Li—Al$_2$O$_3$ (Pt7c) displayed high propene selectivity (around or >99%).

Other tested catalysts of the invention (results not in Table 8 (a)), that were zeolite-based catalyst Pt—Sn-PPh$_3$/Na-ZSM-5 (Pt8c) and Pt—Sn-PPh$_3$/H-ZSM-5 (Pt9c) showed also high selectivities (70-to-90% selectivity) for propylene. The zeolite-based catalysts implied, thus, selectivites for propylene similar to those of the Statoil catalyst (Pt8c; 70-85%), or higher selectivities (Pt9c; 85-90%), and these selectivities were always higher than the selectivities of other commercial catalysts for this reaction (see Table 8 (b) below). Moreover, zeolite-based catalysts Pt—Sn-PPh$_3$/Na-ZSM-5 (Pt8c) and Pt—Sn-PPh$_3$/H-ZSM-5 (Pt9c) were adequate for the obtention of (C$_6$)-aromatic compounds (e.g., benzene and substituted benzenes) (data not shown).

Ni—Sn/Al$_2$O$_3$ (Ni—Sn-PPh/Al$_2$O$_3$ (Ni3)) provided comparable propane selectivities to those achieved using the Pt—Sn benchmark catalysts. As far as known by inventors, this is the first example of selective Ni-catalysed propane dehydrogenation process. The substitution of the expensive Pt systems by earth abundant and cheap Ni systems is very desirable for industrial applications. This example 6 clearly illustrates that nODH of alkanes in which the catalyst compositions of Examples above were employed, provided high conversion indexes as well as very high selectivities for propene.

The selected initial conditions for the non-oxidative dehydrogenation (n-ODH) of 2-butene, butane and 2-butene/butane (1:1) were: temperature, 530° C.; pressure, 1 bar; and gas flow: 3 mL/min of 2-butene or 2-butene/butane (1/1), 21 mL/min of Ar and 1 mL/min $H_2$.

The butane or 2-butene/butane conversion and butane selectivity were determined by gas chromatographic (GC-TCD) analysis of gas samples taken at regular intervals (each 14 min). The response factors of the butane, 2-butene and butadiene were determined using argon as internal standard. The mathematical formula for the determination of the conversion and selectivity are:

$$2\text{ butene/butane conversion (\%)} = \frac{\text{Total 2 butene/butane}_{out}}{\text{Total 2 butene/butane}_{in}} \times 100$$

Butadiene selectivity (%) =

$$\frac{\text{Total butadiene}_{out}}{\text{Total 2 butane/butane}_{in} - \text{Total 2 butane/butane}_{out}} \times 100$$

Next Table 8 (b) lists the results obtained on 2-butene and 2-butene/butane (1:1) dehydrogenation (BDH) by non-oxidative dehydrogenation with some of the catalysts compositions of the invention. Comparative data with the benchmark Statoil catalyst are also included.

TABLE 8b 2-butene and 2-butene/butane (BDH) catalyzed by Pt/Sn-nanocatalyst.

| Name | Composition | C4 feed | Initial conv. -to - conv. After 900 min (%) | Selectivity (%) |
|---|---|---|---|---|
| Pt6c | PtSn-PPh$_3$/Al$_2$O$_3$ | 2-butene | 10.0-to-5.3 | 89 |
| Pt6c | PtSn-PPh$_3$/Al$_2$O$_3$ | 2-butene/butane (1:1) | 4.7-to-4.7 | 93 |

TABLE 8b-continued 2-butene and 2-butene/butane (BDH) catalyzed by Pt/Sn-nanocatalyst.

| Name | Composition | C4 feed | Initial conv. -to - conv. After 900 min (%) | Selectivity (%) |
|---|---|---|---|---|
| Pt25 | PtSn-PPh$_3$/Al$_2$O$_3$ | 2-butene | 12.0 to 4.0 | 89 |
| Pt29 | PtGa-PPh$_3$/Al$_2$O$_3$ | 2-butene | 10 to 1.8 | 88 |

In the non-oxidative dehydrogenation of 2-butene, Pt—Sn—PPh$_3$/Al$_2$O$_3$ (Pt6c) provided the highest initial conversion (10%) and it was progressively deactivated until reaching 5.3% after 900 min of TOS. In terms of product selectivity, the alumina-based catalysts Pt—Sn—PPh$_3$/Al$_2$O$_3$ (Pt6c and Pt25) displayed high butadiene selectivity (around 89%).

In the non-oxidative dehydrogenation of mixtures of 2-butene/butane (1:1), Pt—Sn—PPh$_3$/Al$_2$O$_3$ (Pt6c) provided the highest initial conversion (4.7%) and the conversion remained stable during all the experiment (4.7% conversion after 900 min of TOS). In terms of product selectivity, the alumina-based catalysts Pt—Sn-PPh$_3$/Al$_2$O$_3$ (Pt6c) displayed high butadiene selectivity (around 93%).

Next Table 9 illustrates the data on conversion indexes and selectivity, as well as other parameters of the existing industrial nODH of propane and butene/butane mixtures. Concerning the propane dehydrogenation (PDH), as a whole, data obtained with the catalysts compositions of the invention allow concluding that higher selectivities were obtained (>99%, for the alumina-based) with conversion percentages within those of the commercial Pt-based Oleflex® and Cr-based Catofin® catalysts.

Concerning the 2-butene/butane and 2-butene dehydrogenation (BDH), as a whole, data obtained with the catalysts compositions of the invention allow concluding that significantly higher selectivities were obtained (>99%, for the alumina-based) with conversion percentages within those of the commercial Cr-based Catadiene® catalyst.

TABLE 9

Comparative parameters of current existing industrial processes of nODH of propane.

| Process | Catalyst | Operating Conditions | Conv. (%)/Sel.(%) [1] | License holder |
|---|---|---|---|---|
| Oleflex ® nODH C3 (Sattler et al, 2014, supra) | Pt (1 wt. %)/Al$_2$O$_3$/ Sn (1-2 wt. %)/Na or K(0.1 wt. %) | T = 520-705° C., P = 1.0-3.0 bar | 22-70/ 70-90 | UOP Honeywell |
| Catofin ® nODH C3 (Sattler et al, 2014, supra) | Na or K (0.1 wt. %)/CrOx (20 wt. %)/Al$_2$O$_3$ | T = 575-625° C., P = 0.2-0.5 bar | 35-50/ 50-70 | CB&I Lummus |
| Catadiene ® nODH C4 | Na or K (0.1 wt. %)/CrOx(20 wt. %)/Al$_2$O$_3$ | T = 575-625° C., P = 0.1-0.2 bar | 35-50/ 50-70 | CB&I Lummus |

[1] Percentages of conversion and selectivity provided in the references of the first column Example 7. Synthesis of Catalysts Compositions with Different Organophosporus Compounds Description of the Samples:

There were prepared seven catalysts samples of platinum (Pt)-tin (Sn) catalyst supported onto alumina ($Al_2O_3$) with a nominal Pt and Sn loading of 2.0% w/W and 1.0% w/W (cat0-cat6). The catalysts cat1-cat5 were prepared by decomposition of the organometallic Pt and tin precursors at 100° C. under 3 bar of hydrogen during 40 h in presence of 0.2 equivalents of phosphorous ligands with 6 different functional groups: (Cat1) monophosphine ($PPh_3$) (disclosed in previous examples), (Cat2) diphosphine (dppm), (Cat3) monophosphoramidite (tpd), (Cat4) monophosphite (tppt), (Cat5) secondary phosphine oxide (dpo), and (Cat6) tertiary phosphine oxide (topo). A blank Pt—Sn/$Al_2O_3$ catalyst sample has been prepared in absence of ligand (Cat0).

The results are shown in Table 10, wherein several parameters and features of the obtained catalysts are shown:

provided catalyst with much lower Pt content, Sn content and Sn/Pt molar ratios. Thus, in general, it seems that these functional groups affected the Pt-decomposition rate, the Sn-decomposition rate and the PtSn-nanoparticle mean diameter, but allowed providing nanoparticles around 1.0-2.0 nm of diameter.

3) Monophosphine Cat1 (Already in Previous Examples) Vs. Phosphoramidite Cat3 and Phosphite Cat4:

The difference between these ligands is the different coordination to the metals because of the electronic properties, i.e., phosphines are more basic-donors than phosphoramidites and phosphites, whereas phosphoramidites and phosphites are more n-acceptors than phosphines. It seems that the use of phosphoramidites (cat 3, 1.66 nm) and phosphites (cat 4, 2.63 nm) resulted in larger Pt—Sn nanoparticles than the Pt—Sn stabilized by monophosphines (Cat 1, 1.33 nm). The final Pt content is much lower with phosphoramidites (cat 3, 1.0% wt.) and phosphites (cat 4, 1.4% wt.) than the Pt—Sn stabilized by monophosphines

TABLE 10

| | Cat 0 | Cat 1 | Cat 2 | Cat 3 | Cat 4 | Cat 5 | Cat 6 |
|---|---|---|---|---|---|---|---|
| Functional group | — | Monophosphine | Diphosphine (bidentate ligand) | Phosphoramidite | Phosphite | Secondary phosphine oxyde | Tertiary phosphine oxyde |
| Ligand name | — | TPP (PPh3) | DPPM | TPD | TPPT | DPO | TOPO |
| PtSn—Nanoparticle Mean diameter (nm) | 1.42 ± 0.35 | 1.33 ± 0.31 | Pt—Sn—NPs below detection limit of or electron microscopy (<1 nm). | 1.66 ± 0.28 | 2.63 ± 0.68 | 1.50 ± 0.24 | 2.05 ± 0.53 |
| Pt content by ICP (wt. %) | 1.328 | 1.744 | 1.038 | 1.012 | 1.413 | 0.652 | 0.805 |
| Sn content by ICP (wt. %) | 1.381 | 1.111 | 0.322 | 1.046 | 1.074 | 0.042 | 1.050 |
| Sn/Pt molar ratio (mol/mol) | 1.71 | 1.04 | 0.509 | 1.643 | 1.249 | 0.107 | 2.143 |

TPP (PPh3): Triphenylphosphnine.
DPPM: 1,2-bis(diphenylphosphino)methane.
TPD: Tris(dimethylamino)phosphine.
TPPT: Triphenyl phosphite.
DPO: Diphenylphosphine oxide.
TOPO: Trioctylphosphine oxide 1) Blank Sample Cat0 vs. Ligand Samples Cat 1-5:

In general, blank sample displayed similar mean diameters (1-2 nm) than the samples with ligands (i.e., with organophosphorus compounds). This is because of the stabilizing effect of the alumina support is similar in all the cases. This sample displayed the highest Sn content of all the series (1.3% w/W). This is because of the effect of the ligand on the Sn-decomposition, i.e., the phosphorus ligand somehow reduces the decomposition rate of the Sn-precursor.

2) Monophosphine Cat1 (Already in Previous Examples) Vs. Diphosphine Cat2:

The difference between the monodentate and bidentate ligands is the presence of the stronger coordination of bidentate ligands to the metal because of the chelating effect. The use of diphosphine ligand resulted in small PtSn nanoparticles that even were below the detection limit of the disposable electron microscopy (<1 nm) at the lab of the inventors. This can be rationalized because of the higher stabilization provided by the chelating effect of the ligand on the surface of the PtSn-NPs. The bidentate ligand also (Cat 1, 1.7% wt.), whereas the Sn content is similar in the three cases (i.e., around 1.04-1.11% wt.). Thus, in general, it seems that these functional groups affected the Pt-decomposition rate and the PtSn-nanoparticle mean diameter, but allowed providing nanoparticles around 1.0-3.0 nm of diameter.

4) Monophosphine Cat1 (Already in Previous Examples) Vs. Secondary and Tertiary Phosphine Oxides Cat5 and Cat6:

The difference between these ligands is the absence of lone pair of electrons on the phosphorus (IV) species respect to the previously described P(III) ligands. Thus, it was expected no or very soft interaction with both the metal precursors and the metal nanoparticles. It seems that the use of secondary phosphine oxides (cat 5, 1.50 nm) and tertiary phosphine oxides (cat 6, 2.05 nm) resulted in larger Pt—Sn nanoparticles than the Pt—Sn stabilized by monophosphines (Cat 1, 1.33 nm). The final Pt content is much lower with secondary phosphine oxides (cat 3, 0.6% wt.) and tertiary phosphine oxides (cat 6, 0.8% wt.) than the Pt—Sn stabilized by monophosphines (Cat 1, 1.7% wt.), whereas the final Sn content is much lower with secondary phosphine oxides (cat 3, 0.04% wt.) than those measure with tertirary phosphine oxides (cat 6, 1.05% wt.) and monophosphines (Cat 1, 1.1% wt.). Thus, in general, it seems that these functional groups affected the Pt-decomposition rate, the Sn-decomposition rate and the PtSn-nanoparticle mean diameter but allowed providing nanoparticles around 1.0-3.0 nm of diameter.

General Conclusion:

The use and the nature of ligands applied as additives during the Pt—Sn/Al$_2$O$_3$ catalyst synthesis affected nanoparticle mean diameter and the Pt/Sn composition (i.e., effect on the Pt and Sn-precursors decomposition rate), but allowed to obtain catalyst with nanoparticles of very low diameter (1.0-3.0 nm).

Interestingly too, the data of this example show that by means of the process of the invention (organometallic approach one-pot synthesis) catalyst compositions of Pt—Sn—/Al$_2$O$_3$ could be obtained with nanoparticles of very low diameter (1.42 nm) in a simple and clean process. This supposes an advantage over, for example, other processes of synthesis of these catalysts, such as the one disclosed in EP0328507.

Example 8. Propane Conversion and Selectivity for Propylene in a Poisoned nODH Reaction Using the catalyst composition of the invention PtSn(IV)-PPh$_3$@Al2O3, abbreviated PtSnIV-P in FIG. 7, the propane dehydrogenation (PDH) as in previous Example 6 (Table 8 (a)) was performed in the presence of poison of CO2 (empty circles, PtSn$^{IV}$-P CO$_2$) or without the poison (solid circles, PtSn$^{IV}$-P). X-axis shows time on stream reaction in hours of the catalyst.

Figure 7:
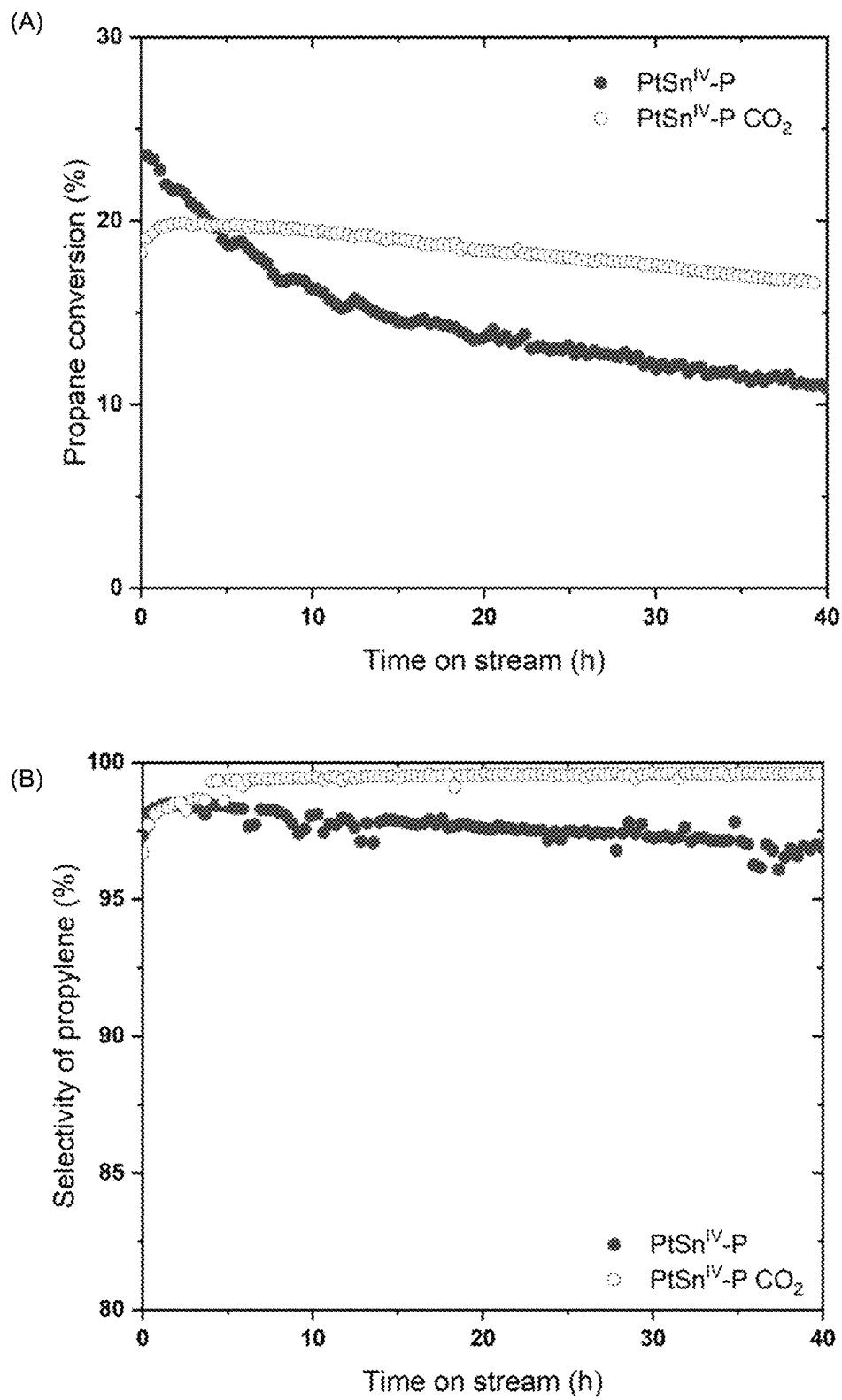
FIG. 7 illustrates in (A) the percentage (%) of propane conversion, and in (B) the percentage (%) of selectivity for propylene in a nODH of propane (PDH) comparing using in the stream a poisoning molecule, $CO_2$, or no poisoning. Empty circles show results along time (X-axis in hours) of the reaction in the presence of poisoning. Solid circles show the results without poisoning.

As illustrated in FIG. 7 (A), with the percentage (%) of propane conversion, and (B) with the percentage (%) of selectivity for propylene, by introducing CO$_2$ poisoning (empty circles in FIGS. 7 (A) and (B)) the catalyst improves in stability, meaning that propane conversion is more stable along time than without poisoning, while the selectivity for propylene is also improved.

Little is known about the catalytic performance of industrial catalysts in the presence of poisons. Indeed, the presence of oxygenated or sulfuric molecules in the feed act as depressants for Pt—Sn catalysts, killing their active sites, and leading to deactivation of the catalyst and to low selectivity toward the desired products. The use of water and oxygenates substrates at low levels in the propane feed has been reported. At higher levels, these impurities can poison the catalysts by various mechanisms. For example, they can deplete chlorine essential for redispersion of sintered platinum from the catalyst and increase the selectivity to carbon oxides. Although the presence of these species are considered to negatively affect catalytic activity, their use in appropriate amounts, could benefit catalytic performance, by reducing the formation of coke and increasing the yield towards propylene. No studies are reported in literature concerning the poisoning of Pt—Sn catalysts in the presence of CO2 and sulfur.

Further aspects/embodiments of the present invention can be found in the following clauses:

Clause 1.—A catalyst composition comprising:
(a) a metallic nanoparticle; and
(b) a porous support with a surface area; wherein the nanoparticle (a) is adsorbed on the surface area of the porous support;

wherein the nanoparticle (a) comprises (i) one or more metallic elements of group 10 of the periodic table; (ii) one or more organic molecules selected from the group consisting of an organophosphorus compound, and an N-heterocyclic carbene; and (iii) one or more metallic elements selected from the group consisting of tin (Sn), gallium (Ga), and indium (In).

Clause 2.—The catalyst composition according to clause 1, wherein at least one of the elements of group 10 in the nanoparticle is platinum (Pt) or nickel (Ni)

Clause 3.—The catalyst composition according to any one of clauses 1-2, wherein the tin (Sn), gallium (Ga) and indium (In) are in the nanoparticles (a), and onto the surface area of the porous support (b).

Clause 4.—The catalyst composition according to any one of clauses 1-3, further comprising one or more catalyst promoters.

Clause 5.—The catalyst composition according to any one of clauses 1-4, wherein the percentage by weight of the one or more metallic element of group 10 is from 0.2 to 5.0%, and the percentage by weight of the one or more organic molecule selected from the group consisting of an organophosphorus compound and an N-heterocyclic carbene is from 0.05 to 0.2%, all percentages in relation with the total weight of catalyst composition.

Clause 6.—The catalyst composition according to clause 5, wherein the Sn, Ga, and In, are present in a percentage by weight from 0.15 to 1.0%, all percentages in relation with the total weight of catalyst composition.

Clause 7.—The catalyst composition according to any one of clauses 1-6, wherein the metallic nanoparticle has a diameter from 1.0 to 15.0 nm measured by Transmission Electronic Microscopy (TEM).

Clause 8.—The catalyst composition according to any one of clauses 1-7, wherein the specific surface area (in m$^2$/g), according to BET theory, is from 100 to 500 m$^2$/g.

Clause 9.—The catalyst composition according to any one of clauses 1-8, wherein the mole ratio of the one or more organic molecules and the total of the one or more of the metallic elements is of 0.05-0.25:1.

Clause 10.—The catalyst composition according to any one of clauses 1-9, wherein the porous support is selected from an alumina-based porous material, a silica-based porous material, zeolite-based porous material, aluminosilicate-based porous material, and combinations thereof.

Clause 11.—A process for preparing a catalyst composition as defined in any one of clauses 1-10, comprising in a one-pot step, the decomposition of one or more organometallic precursor compounds of one or more elements of group 10, and the decomposition of one or more organometallic precursors compounds of one or more metallic elements selected from the group consisting of tin (Sn), gallium (Ga), and indium (In), in the presence of an organic solvent, a porous support, and of one or more organic molecules selected from the group consisting of an organophosphorus compound and an N-heterocyclic carbene; the one-pot decomposition carried out at a temperature from 20° C. (r.t) to 100° C. for a period from 30 minutes to 70 hours, and at a pressure from $1.0 \times 10^5$ Pa to $5.0 \times 10^5$ Pa in hydrogen gas atmosphere.

Clause 12—The process according to clause 11, wherein the one or more organometallic precursor compounds are added in an amount of 1 mole per 0.1-1.0 mole of the one or more organic molecule selected from the group consisting of an organophosphorus compound, and an N-heterocyclic carbene.

Clause 13.—A process for producing one or more ($C_2$-$C_4$)-alkenes, and/or one or more ($C_6$)-aromatic compounds, the process comprising a non-oxidative dehydrogenation of an ($C_2$-$C_4$)-alkane and/or of an ($C_3$-$C_4$)-alkene or, for the production of the one or more ($C_6$)-aromatic compounds a non-oxidative dehydrogenation of an ($C_2$-$C_4$)-alkane and/or a non-oxidative dehydrogenation of a ($C_6$)-cycloalkane compound, said dehydrogenations carried out with a step of contacting a feed stream comprising the ($C_2$-$C_4$)-alkane and/or the ($C_3$-$C_4$)-alkene, or the ($C_2$-$C_4$)-alkane and/or the ($C_6$)-cycloalkane with the catalyst composition as defined in any one of clauses 1-10, to obtain the one or more alkenes and/or the one or more aromatic compounds.

Clause 14.—The process according to clause 13, wherein the ($C_2$-$C_4$)-alkane is propane and the ($C_2$-$C_4$)-alkene is propylene.

Clause 15.—Use of the catalyst composition as defined in any one of clauses 1-10, in non-oxidative propane dehydrogenation (PDH), non-oxidative butane-butene dehydrogenation (BDH), and propane aromatization.

CITATION LIST

Patent Literature

EP0328507A1 (Fina Research)
US2005003960 (STATOIL ASA)

Non Patent Literature

Sattler et al. 2014. Catalytic Dehydrogenation of Light Alkanes on Metals and Metal Oxides. *Chemical Reviews* vol. no. 114, pp: 10613-10653

Searles et al. 2018. Highly Productive Propane Dehydrogenation Catalyst Using Silica-Supported Ga—Pt Nanoparticles Generated from Single-Sites. *Journal of American Chemical Society* 140, pp.: 11674-11679

Wang et al. 2017. Colloidal Synthesis of Pt—In Bimetallic nanoparticles for Propane Dehydrogenation. *Can. J. Chem* 1-29

Lomelí-Rosales et al. 2019. A general one-pot methodology for the preparation of mono and bimetallic nanoparticles supported on carbon nanotubes: application in the semi-hydrogenation of alkynes and acetylene. Chem. Eur. J. 10.1002/chem.201901041

Humlot and Basset. et al. (1998). Surface Organometallic Chemistry on Metals: Formation of a Stable: Sn (n-C4H9) Fragment as a Precursor of Surface Alloy Obtained by Stepwise Hydrogenolysis of Sn (n-C4H9) 4 on a Platinum Particle Supported on Silica. *J. Am. Chem. Soc.* 120, 1, 137-146

Bjørgen et al. (2008), Methanol to gasoline over zeolite H-ZSM-5: Improved catalyst performance by treatment with NaOH. *Applied Catalys A: General* 345, 43-50

Rouge et al. (2019). A smarter approach to catalysts by design: Combinig surface organometallic chemistry on oxide and metal gives selective catalysts for dehydrogenation of 2,3-dimethylbuthane. *Molecular Catalysis* 471, 21-26

The invention claimed is:
1. A catalyst composition comprising:
(a) a metallic nanoparticle; and
(b) a porous support with a surface area: wherein the nanoparticle (a) is adsorbed on the surface area of the porous support;

wherein the nanoparticle (a) comprises
(i) one or more metallic elements of group 10 of the periodic table;
(ii) one or more organic molecules selected from the group consisting of an organophosphorus compound and an N-heterocyclic carbene; and
(iii) one or more metallic elements selected from the group consisting of tin (Sn), gallium (Ga), and indium (In).

2. The catalyst composition according to claim 1, wherein the organophosphorus compound is a compound of formula (I)

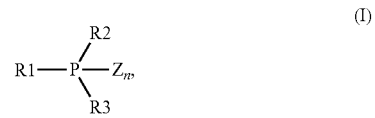

wherein n is an integer 0 or 1, and when n is 1, Z is oxygen (=O); and
wherein R1, R2 and R3 are each independently selected from the group consisting of:
($C_1$-$C_{10}$)-alkyl, ($C_1$-$C_4$)-alkoxyl, ($C_1$-$C_4$)-alkanoyl, ($C_1$-$C_4$)-alkoxycarbonyl and ($C_1$-$C_4$)-alkanoyloxy, all of them be construed as straight or branched,
phenyl optionally substituted;
a radical represented by —C—P(R4)(R5), wherein R4 and R5 are each independently selected from hydrogen (H) and phenyl optionally substituted;
a radical represented by —N(R6)(R7), wherein R6 and R7 are each independently selected from the group consisting of ($C_1$-$C_{10}$)-alkyl, ($C_1$-$C_4$)-alkoxyl, ($C_1$-$C_4$)-alkanoyl, ($C_1$-$C_4$)-alkoxycarbonyl and ($C_1$-$C_4$)-alkanoyloxy, all of them construed as straight or branched; and
a radical —O— R8, wherein R8 is a C6-aromatic ring optionally substituted.

3. The catalyst composition according to wherein R1, R2 and R3 are each independently selected from the group consisting of:
($C_1$-$C_{10}$)-alkyl, ($C_1$-$C_4$)-alkoxyl, ($C_1$-$C_4$)-alkanoyl, ($C_1$-$C_4$)-alkoxycarbonyl and ($C_1$-$C_4$)-alkanoyloxy, all of them construed as straight or branched,
phenyl optionally substituted;
a radical represented by —C—P(R4)(R5), wherein R4 and R5 are each independently selected from hydrogen (H) phenyl and phenyl optionally substituted; and
a radical represented by —N(R6)(R7), wherein R6 and R7 are each independently selected from ($C_1$-$C_{10}$)-alkyl, ($C_1$-$C_4$)-alkoxyl, ($C_1$-$C_4$)-alkanoyl, ($C_1$-$C_4$)-alkoxycarbonyl and ($C_1$-$C_4$)-alkanoyloxy, all of them construed as straight or branched.

4. The catalyst composition according to claim 1, wherein the organophosphorus compound is selected from the group consisting of triphenylphosphine, 1,2-bis(diphenylphosphino)methane, tris(dimethylamino)phosphine, diphenylphosphine oxide, and trioctylphosphine oxide.

5. The catalyst composition according to claim 2, wherein the organophosphorus compound is a compound of formula (I), which is a phosphite in which n is 0 and wherein R1, R2 and R3 are each a radical —O—R8, wherein R8 is a C6-aromatic ring optionally substituted.

6. The catalyst composition according to claim 5, wherein the compound of formula (I) is triphenylphosphite.

7. The catalyst composition according to claim 1, wherein at least one of the elements of group 10 in the nanoparticle is platinum (Pt) or nickel (Ni).

8. The catalyst composition according to claim 1, wherein the tin (Sn), gallium (Ga) and indium (In) are in the nanoparticles (a) and on the surface area of the porous support (b).

9. The catalyst composition according to claim 1, further comprising one or more catalyst promoters.

10. The catalyst composition according to claim 1, wherein the percentage by weight of the one or more metallic element of group 10 is from 0.2 to 5.0%, and the percentage by weight of the one or more organic molecule selected from the group consisting of an organophosphorus compound and an N-heterocyclic carbene is from 0.05 to 0.2%, all percentages in relation with the total weight of catalyst composition.

11. The catalyst composition according to claim 10, wherein the Sn, Ga, and In are present in a percentage by weight from 0.15 to 1.0%, all percentages in relation with the total weight of catalyst composition.

12. The catalyst composition according to claim 1, wherein the metallic nanoparticle has a diameter from 0.5 to 15 nm, measured by Transmission Electronic Microscopy (TEM).

13. The catalyst composition according to claim 1, wherein the specific surface area (in $m^2/g$), according to BET theory, is from 100 to 500 $m^2/g$.

14. The catalyst composition according to claim 1, wherein the mole ratio of the one or more organic molecules and the total of the one or more of the metallic elements is of 0.05-0.25:1.

15. The catalyst composition according to claim 1, wherein the porous support is selected from the group consisting of an alumina-based porous material, a silica-based porous material, zeolite-based porous material, aluminosilicate-based porous material, and combinations thereof.

16. A process for preparing a catalyst composition as defined in claim 1, comprising in a one-pot step, the decomposition of one or more organometallic precursor compounds of one or more elements of group 10, and the decomposition of one or more organometallic precursors compounds of one or more metallic elements selected from the group consisting of tin (Sn), gallium (Ga), and indium (In), in the presence of an organic solvent, a porous support, and of one or more organic molecules selected from the group consisting of an organophosphorus compound and an N-heterocyclic carbene: the one-pot decomposition carried out at a temperature from 20° C. (r.t) to 100° C. for a period from 30 minutes to 70 hours, and at a pressure from $1.0 \times 10^5$ Pa to $5.0 \times 10^5$ Pa in hydrogen gas atmosphere.

17. The process according to claim 16, wherein the one or more organometallic precursor compounds are added in an amount of 1 mole per 0.1-1.0 mole of the one or more organic molecules selected from the group consisting of an organophosphorus compound and an N-heterocyclic carbene.

18. The process according to claim 16, wherein the organophosphorus compound is a compound of formula (I)

(I)

wherein n is an integer 0 or 1, and when n is 1, Z is oxygen (═O); and wherein R1, R2 and R3 are each independently selected from the group consisting of:
($C_1$-$C_{10}$)-alkyl, ($C_1$-$C_4$)-alkoxyl, ($C_1$-$C_4$)-alkanoyl, ($C_1$-$C_4$)-alkoxycarbonyl and ($C_1$-$C_4$)-alkanoyloxy, all of them be construed as straight or branched,
phenyl optionally substituted;
a radical represented by —C—P(R4)(R5), wherein R4 and R5 are independently selected from hydrogen (H) and phenyl optionally substituted;
a radical represented by —N(R6)(R7), wherein R6 and R7 are each independently selected from ($C_1$-$C_{10}$)-alkyl, ($C_1$-$C_4$)-alkoxyl, ($C_1$-$C_4$)-alkanoyl, ($C_1$-$C_4$)-alkoxycarbonyl and ($C_1$-$C_4$)-alkanoyloxy, all of them construed as straight or branched; and
a radical —O—R8, wherein R8 is a $C_6$-aromatic ring optionally substituted.

19. A process for producing one or more ($C_2$-$C_4$)-alkenes, and/or one or more ($C_6$)-aromatic compounds, the process comprising a non-oxidative dehydrogenation of an ($C_2$-$C_4$)-alkane and/or of an ($C_3$-$C_4$)-alkene or, for the production of the one or more ($C_6$)-aromatic compounds a non-oxidative dehydrogenation of an ($C_2$-$C_4$)-alkane and/or a non-oxidative dehydrogenation of a ($C_6$)-cycloalkane compound, said dehydrogenations carried out with a step of contacting a feed stream comprising the ($C_2$-$C_4$)-alkane and/or the ($C_3$-$C_4$)-alkene, or the ($C_2$-$C_4$)-alkane and/or the ($C_6$)-cycloalkane with the catalyst composition as defined in claim 1, to obtain the one or more alkenes and/or the one or more aromatic compounds.

20. The process according to claim 19, wherein the ($C_2$-$C_4$)-alkane is propane and the ($C_2$-$C_4$)-alkene is propylene.

21. A method of using-the catalyst composition as defined in claim 1, in non-oxidative propane dehydrogenation (PDH), non-oxidative butane-butene dehydrogenation (BDH), or propane aromatization.

* * * * *